(12) United States Patent
Gavlak et al.

(10) Patent No.: US 9,089,801 B1
(45) Date of Patent: Jul. 28, 2015

(54) MANIFOLD AND STRAINER ASSEMBLY

(71) Applicant: Denali Medical Concepts, LLC, Chamblee, GA (US)

(72) Inventors: William Gavlak, Atlanta, GA (US); Roger Wessels, Fayetteville, GA (US); Roland Krevitt, Scotts Valley, CA (US)

(73) Assignee: Denali Medical Concepts, LLC, Chamblee, GA (US)

( * ) Notice: Subject to any disclaimer, the term of this patent is extended or adjusted under 35 U.S.C. 154(b) by 0 days.

(21) Appl. No.: 14/707,619

(22) Filed: May 8, 2015

Related U.S. Application Data

(63) Continuation-in-part of application No. 13/291,192, filed on Nov. 8, 2011, now Pat. No. 9,056,158.

(51) Int. Cl.
*B01D 29/44* (2006.01)
*B01D 29/90* (2006.01)
*A61M 1/00* (2006.01)
*B01D 35/28* (2006.01)

(52) U.S. Cl.
CPC ............. *B01D 35/28* (2013.01); *A61M 1/0001* (2013.01); *A61M 1/0015* (2014.02); *A61M 1/0056* (2013.01); *B01D 29/44* (2013.01); *B01D 29/908* (2013.01); *A61M 2205/7545* (2013.01); *A61M 2206/16* (2013.01); *B01D 2201/301* (2013.01); *B01D 2201/309* (2013.01)

(58) Field of Classification Search
CPC . A61M 1/001; A61M 1/0015; A61M 1/0056; A61M 2205/6081; A61M 2205/7545; A61M 2206/16; B01D 29/014; B01D 29/0095; B01D 29/0097; B01D 29/44; B01D 29/90; B01D 29/908; B01D 35/143; B01D 35/30; B01D 27/101; B01D 2201/301; B01D 2201/309; B01D 2201/52; B01D 35/28
See application file for complete search history.

(56) References Cited

U.S. PATENT DOCUMENTS

| | | | |
|---|---|---|---|
| D249,541 S * | 9/1978 | Cattano, Sr. | D23/209 |
| 4,411,783 A * | 10/1983 | Dickens et al. | 210/304 |
| 4,588,426 A * | 5/1986 | Virgille et al. | 55/337 |
| 4,655,754 A | 4/1987 | Richmond et al. | |
| D342,306 S * | 12/1993 | Young | D23/210 |
| 5,792,126 A * | 8/1998 | Tribastone et al. | 604/319 |
| 5,997,733 A | 12/1999 | Wilbur et al. | |
| 6,180,000 B1 | 1/2001 | Wilbur et al. | |
| 6,222,283 B1 | 4/2001 | Regla | |
| 6,331,246 B1 | 12/2001 | Beckham et al. | |
| 6,902,673 B2 | 6/2005 | Smit et al. | |
| 7,163,618 B2 | 1/2007 | Beckham et al. | |
| 7,497,340 B2 | 3/2009 | Hershberger et al. | |
| 7,615,037 B2 | 11/2009 | Murray | |
| 7,621,898 B2 | 11/2009 | Lalomia et al. | |
| 2004/0016691 A1* | 1/2004 | Smit et al. | 210/304 |
| 2006/0236913 A1* | 10/2006 | Wills | 116/206 |
| 2010/0297577 A1* | 11/2010 | Cohen | 433/92 |

* cited by examiner

*Primary Examiner* — David C Mellon
(74) *Attorney, Agent, or Firm* — David L. King

(57) ABSTRACT

A waste collection manifold assembly 10 has a housing 13 and a strainer 80. The housing 13 has at least one input port 12A, 12B, 12C, 12D for receiving waste collection products 1 through a vacuum line 4. The housing 13 includes an interior chamber 11 for receiving the waste collection products 1 and a fluid discharge port 14 for passing fluids 6 into a waste collection unit 2. The strainer 80 is located in the chamber 11 and above the fluid discharge port 14. The at least one inlet port 12A, 12B, 12C, 12D is positioned to open alongside an interior chamber wall 13A of the housing 13 above the strainer 80 to direct the flow of the waste collection products 1 in a downward swirl along the interior chamber wall 13A toward the strainer 80.

25 Claims, 23 Drawing Sheets

MANIFOLD AND STRAINER ASSEMBLY

RELATED APPLICATIONS

This application is a continuation in part of U.S. application Ser. No. 13/291,192 filed Nov. 8, 2011 entitled "Improved Manifold & Strainer Assembly".

TECHNICAL FIELD

The present invention relates generally to a manifold and strainer assembly and more particularly to a manifold and peg strainer assembly for use with a waste collection unit to direct and separate solid medical waste material from entering the waste collection unit.

BACKGROUND OF THE INVENTION

There are a number of manifold and filtration devices used in combination with commercially available medical waste collection systems.

In U.S. Pat. No. 7,497,340 the inventors recite a list of medical waste collection units. Examples of waste collection units can be found in U.S. Pat. Nos. 5,997,733; 6,180,000; and 6,222,283. For instance, U.S. Pat. No. 5,997,733 discloses a waste liquid and smoke disposal system which combines the functions of a smoke extraction system and a waste collection unit, typically in, but not limited to, a surgical environment. The smoke extraction system and the waste collection unit are connected to supply the medical waste collected thereby to a waste treatment (e.g. decontamination and/or sterilization) and disposal system. In such systems, the waste collection unit can be provided as a cart-mounted apparatus to provide mobility. The waste collection unit can then dock to known docking stations to dispose of the medical waste collected by the unit. As a result, surgical teams can quickly, easily, and efficiently maintain the integrity of a surgical site with a minimum of operating components.

Disposable manifold and filter assemblies are used to facilitate the collection of the medical waste into the waste collection unit. Typically, the manifold and filter assembly includes at least one filter to remove solid or semi-solid material such as bone chips, flesh, blood clots or the like from the liquid medical waste generated by the surgical procedure or operation. Preferably, the single use manifolds are disposed of between patients, or when the manifold is spent, i.e., filled with solid and semi-solid materials. An example of a disposable manifold for use in waste collection units is described in U.S. Pat. No. 6,331,246 to Beckham et al. This Beckham et al patent discloses a manifold and filter assembly for use with a waste collection unit to filter medical waste generated during a medical process. The manifold and filter assembly includes a manifold housing, inlet ports, an outlet port, and a series of filters disposed between the inlet and outlet ports. The filters retain solid and semi-solid materials from a fluid carrier entering the manifold housing through the inlet ports. Check valves are placed on the inlet ports to establish unidirectional flow. Currently, once the filters are plugged with debris, the manifold housing begins to fill with the medical waste. The check valves ensure that the medical waste does not reverse flow into the inlet ports.

One of the first medical waste collection units was a product called the Neptune® Waste Management System, a commercially available waste collection and disposal device. The Neptune® System was designed and manufactured by a company called American Immuno Tech, Costa Mesa, Calif., and Stryker® eventually acquired the product from American Immuno Tech and all patents and IP became property of Stryker®.

The Neptune® System has an independent vacuum pump on the unit which suctions fluid from a surgical field and collects it in a large 20 Liter canister which is later disposed of following a surgical procedure. The Neptune® System is typically used in high fluid procedures such as arthroscopies. A "single use" fluid manifold is used in conjunction with the Neptune® System to filter solid particulate matter from the liquid so the canister does not become overburdened with debris.

American Immuno Tech was granted a patent for an original manifold design on Dec. 18, 2001. This manifold, of U.S. Pat. No. 6,331,246, can be clogged very badly as a result of a poor design. Specifically, the "Duck Billed" anti-reflux valves located on the manifold ports clogged causing Neptune® System to lose vacuum pressure. If the manifold body got too full of debris, the Neptune® System could lose all vacuum pressure and render the entire system useless.

Improvements were made to the original '246 manifold design by a company called Stryker® and the later versions worked better and clogged less. One of the new manifolds is disclosed in U.S. Pat. No. 7,163,618.

In February of 2004 a next generation, third manifold was introduced to the market by Stryker®. It was of a completely different design than the previous two versions of manifolds and performed well. This third manifold was awarded a grant of U.S. Pat. No. 7,497,340.

Additionally, a forth manifold was introduced by Stryker® which has a single port on the manifold body so only one suction line can be attached to the manifold versus the four ports on all other designs. This manifold was called "The Single Port" manifold and was offered to the market as a cost savings alternative to the four port options. A patent was granted for this design, U.S. Pat. No. 6,902,673.

All of these prior art manifolds suffer from high levels of design complexity and require numerous components adding to cost. When disposable devices, best suited for single use, cost too much there is a tendency for the end user to want to clean and reuse the device. These prior art manifolds by having so many separate plastic molded parts assembled together results in increased material weight and cost.

A more important issue is when the multiport manifold with filtration devices clogs a potential risk exists where the multiport vacuum ports reverse flow causing the waste fluids to back into the vacuum lines and into an open surgical site. As repulsive as this seems it is also very dangerous from a contamination perspective.

This is a real concern and has led to numerous design changes in multiport manifolds. In U.S. Pat. No. 7,497,340 a bypass is included to prevent medical waste from reaching the inlet ports. By providing this fluid bypass, the manifold and filter assembly of this prior art invention eliminates the backup of the medical waste to the inlet thereby allowing the medical waste to continually flow through the manifold and filter assembly even when the manifold and filter assembly is spent, i.e., the filter basket is filled. The filter basket includes a plurality of openings to filter the medical waste in the fluid path between the inlet and the outlet. The plurality of inlet ports has ends that are centrally located aligned in a horizontal row spaced above the basket and the waste products drop into the basket to be filtered. The filter basket is spaced from the manifold housing to create a fluid bypass between the filter basket and the manifold housing. The fluid bypass is in fluid communication with the outlet whereby the excess medical waste can overflow over the peripheral wall to the outlet through the fluid bypass when the filter is full and virtually useless.

This prior art design has an end cap that can be reopened and the contents of the filter basket dumped and the cap easily snapped back on means it is tempting to reuse this device. Reuse is exacerbated by the high cost of this multiport design. More importantly, the overfilling of the filter basket is common as the device is so costly it is desirable to completely fill the basket before replacing it. This means unfiltered debris is going directly into the collection unit.

It is therefore an object of the present invention to greatly increase the volume of debris a multiport manifold can retain without blocking the device. A further object is to insure the device is difficult to reuse. Another objective is to provide a positive indication that the device has been previously used.

Other objectives are to simplify the design, reduce the raw material and components needed to manufacture the device, provide the device at a low cost for single use and to make it so inexpensive it would be foolish to attempt to reuse it.

These and other objectives are achieved by the device and described as follows.

SUMMARY OF THE INVENTION

A waste collection manifold assembly has a housing and a strainer. The housing has at least one input port for receiving waste collection products through a vacuum line. The housing has an interior chamber for receiving the waste collection products and a fluid discharge port for passing fluids into a waste collection unit. The strainer is located in the chamber and above the fluid discharge port. At least one inlet port is positioned to open alongside an interior chamber wall of the housing above the strainer to direct the flow of the waste collection products in a downward swirl along the interior chamber wall toward the strainer. The strainer has a plurality of upwardly extending peg projections extending from a conically shaped base with a center opening. The upwardly extending peg projections are aligned in a plurality of first and second radial rows extending from the center opening toward the chamber wall. One second row being interposed between and adjacent each pair of first rows. The peg projections of the first rows extending outwardly from the center opening further than the peg projections of the second rows. The first rows extending closer to the chamber wall than the second rows to form inlet channels of varying size around the circumference of the strainer. The center opening extends inwardly through a hollow cylinder, the hollow cylinder fitting into the discharge port, and the strainer further has a debris blocking tubular cylindrical net reinforced by a coiled reinforcing member affixed over the central opening.

The waste collection manifold further has a non-removable end cap with a locking means for attachment to the housing. The housing has an open chamber end with a complimentary locking means for accepting the end cap and making a permanent attachment to seal the open chamber end. The locking means of the end cap is a projecting lip ring and the locking means of the housing is a complimentary groove each having mating surfaces inclined to snap locking together on assembly. The end cap further has a plurality of arcuate stiffening ribs projecting downwardly from the end cap, each rib being spaced from the locking means a distance sufficient to position the housing wall between the stiffening ribs and the locking means of the end cap. The stiffening ribs prevent the housing wall from collapsing under vacuum.

The housing has a circular shape when viewed in cross section. The chamber portion of the housing is either cylindrical or conically tapered narrowing toward the direction of the discharge port. The interior chamber walls form a smooth surface to facilitate waste collection flow to the strainer. The preferred housing has two or more inlet ports. Preferably, the two or more inlet ports are vertically spaced. The two or more vertically spaced inlet ports are circumferentially aligned, forming a stacked row of inlet ports. The most preferred embodiment of the waste collection manifold assembly has four inlet ports. Each of the at least one inlet ports has a chamber end extending to the interior chamber wall. The interior chamber wall formed with a smooth interior cylindrical or conical surface and the chamber end of each inlet port is flush to the interior surface of the chamber. Each of the at least one inlet ports are inclined downwardly relative to a horizontal plane by about 3 degrees or more relative to a horizontal plane. The strainer has a plurality of upwardly extending peg projections extending from a conically shaped base with a center opening. The upwardly extending peg projections are aligned in radial rows extending from the center opening toward the chamber wall. The rows are linear or could be optionally curved. The rows of peg projections extend outwardly to an end spaced from the chamber interior surface to form a flow channel between the chamber wall and the outermost peg projections. This flow channel is a circumferentially continuous void extending 360 degrees between the wall and the strainer. The adjacent rows of peg projections form radial flow channels tapering from wide at the intersection with the circumferential channel at the radially outer end and narrowing toward the radially inner end adjacent to the center opening, the tapering radial flow channels entrapping debris. The plurality of projecting projections are round pegs spaced and aligned in rows. The pegs are of equal lengths vertically oriented such that the plurality of pegs form a truncated upper conical shape high at the outer periphery of pegs and dipping lower toward the center opening. The pegs have a round or circular cross section of an average diameter (d) and a length (L) wherein the pegs form a substantially rigid debris barrier open to fluid flow between adjacent pegs.

The center opening extends inwardly through a hollow cylinder, the hollow cylinder fitting into the discharge port. The discharge port has an internal locking ring and the hollow cylinder has a split locking ring that complimentarily locks together upon assembly of the strainer to the housing.

The waste collection manifold assembly has an assembly of tethered covers including a plurality of tethered inlet port covers, one for each inlet port, and a tethered single discharge port cover for sealing the discharge port. The assembly of tether covers is neatly staked to a meltable projection on the housing, securing the tether cover assembly to the housing.

The waste collection manifold assembly further has a tamper proof prior-use indicator device, the prior-use indicator being internally affixed to the interior surface in the chamber of the housing, the indicator device changes color when exposed to moisture; and wherein the housing is clear or at least translucent so the color change is readily observable. The prior-use indicator irreversibly changes from a first color to red upon exposure to moisture.

The waste collection manifold assembly is sealed upon assembly by the end cap and the tethered ports or otherwise packaged to prevent premature exposure to moisture sufficient to prematurely activate the prior-use indicator. The prior-use indicator's visible exterior location on the housing is encircled by a label that is open in the area over the prior-use indicator to draw attention to the prior-use condition and the label has a "single use warning" printed on the label.

DEFINITIONS

As used herein and in the claims:

"debris" as used herein means particulate waste products including bone chips, tissue, muscle, cartilage and blood clots in solid or semi-solid form.

"fluids" as used herein means any liquid waste including wound irrigation fluids, blood and non-solid flowable matter.

"waste collection products" means any combination of debris or fluids that can be sucked through vacuum lines and collected in a manifold housing or passed into a waste collection container through a manifold.

BRIEF DESCRIPTION OF THE DRAWINGS

The invention will be described by way of example and with reference to the accompanying drawings in which.

DETAILED DESCRIPTION OF THE INVENTION

Figure 23:
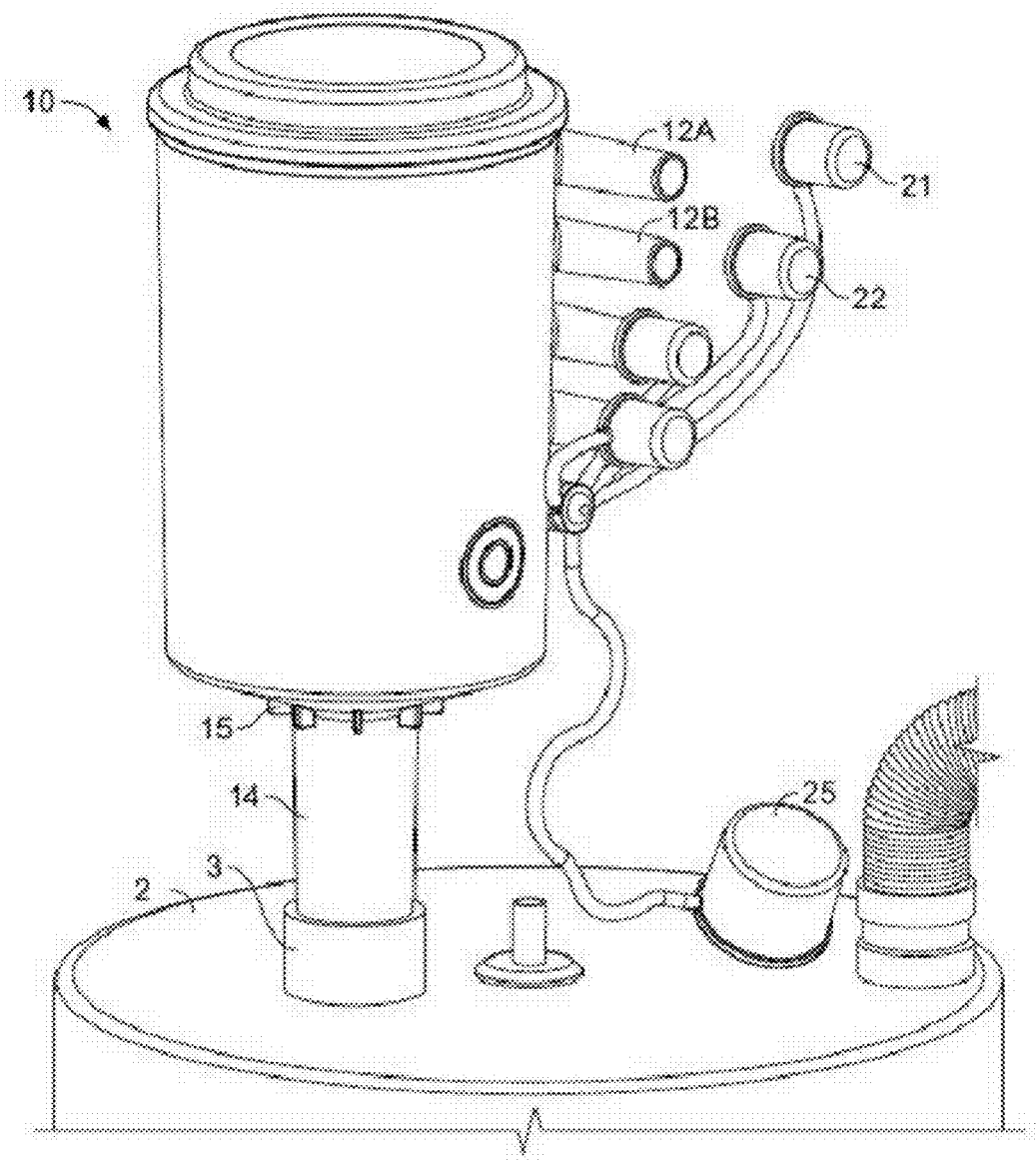
FIG. 23 is a view of the device inserted into a receiving opening of a collection device.
Figure 24:
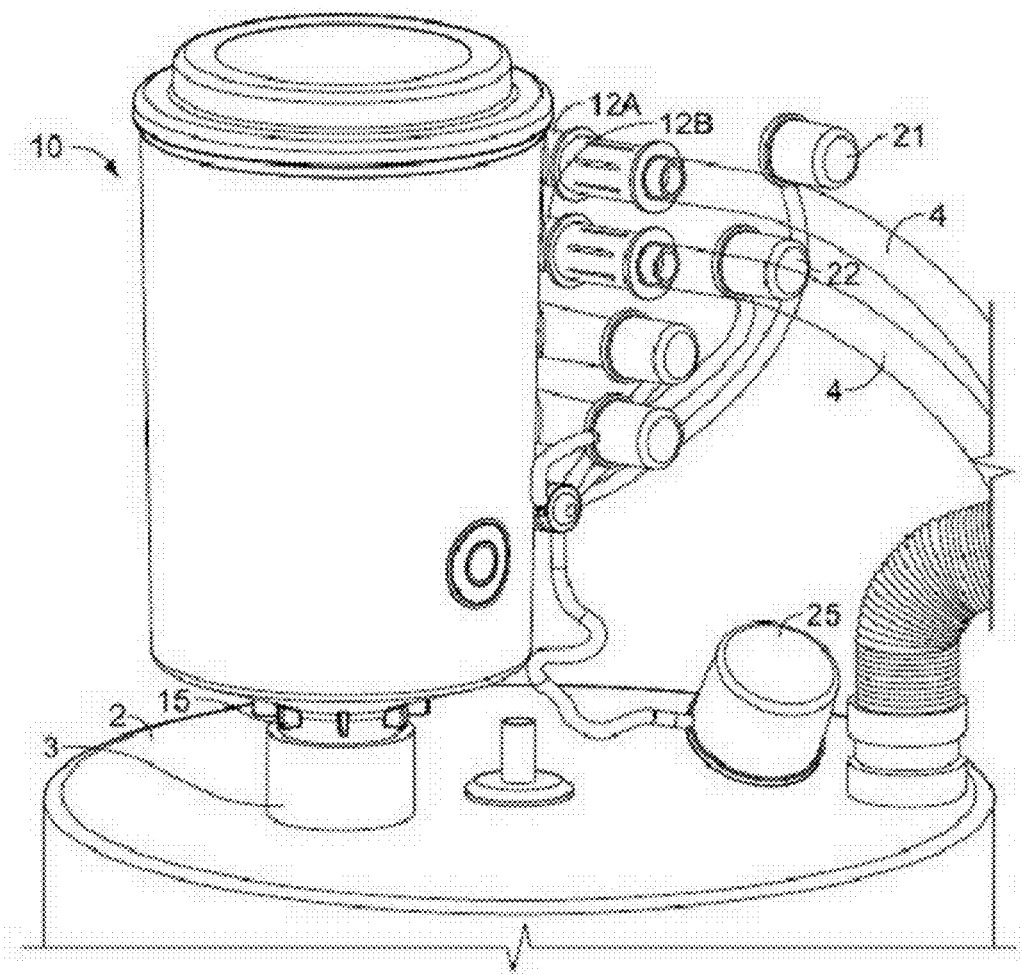
FIG. 24 is the multi-port manifold device with two clear vacuum lines attached to the collection unit.
Figure 25:
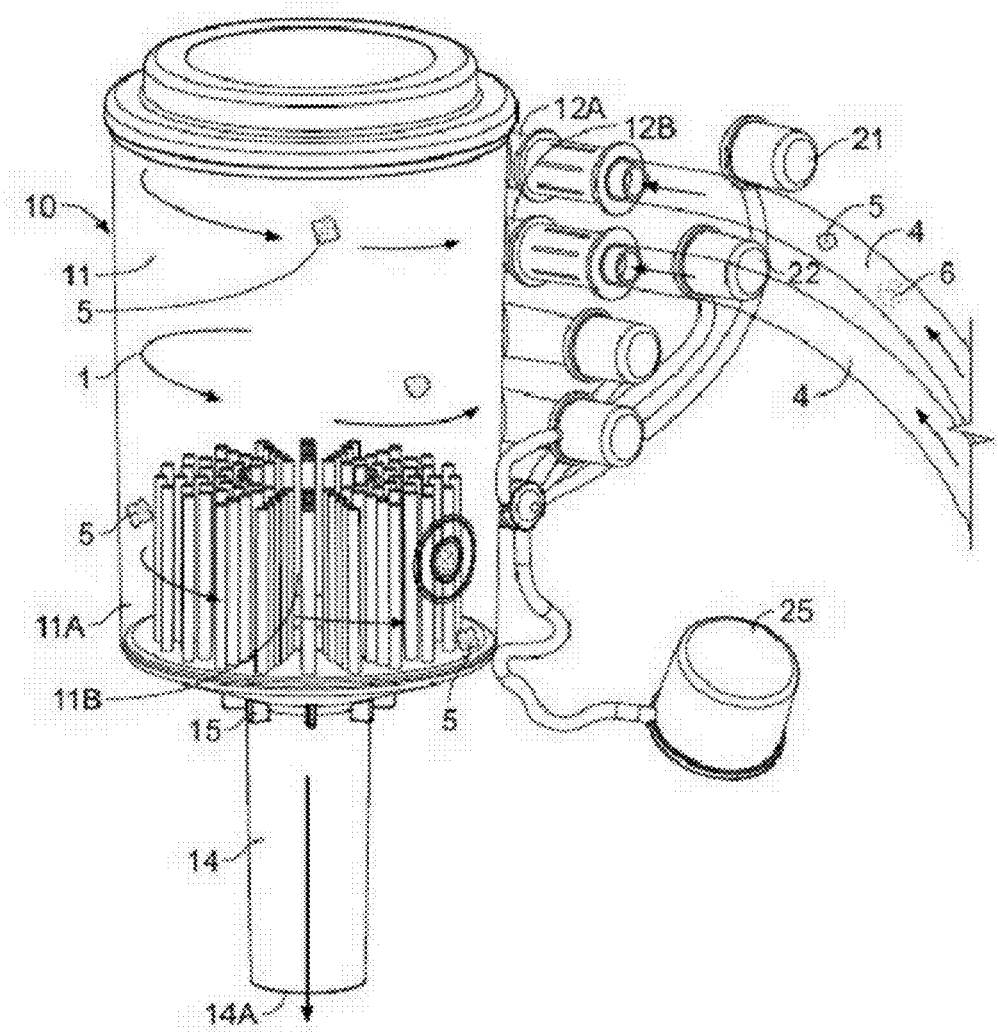
FIG. 25 is a view showing the flow path, the waste collection products of fluid and debris being swirled into the manifold housing and captured on the peg strainer assembly.

With reference to FIGS. 1-30, the various components of the improved manifold strainer assembly 10 are illustrated. These views illustrate the entire assembly 10 and also elemental features of the assembly in great detail. To better understand the inventions use, FIGS. 23-25 illustrate the improved manifold assembly 10 in use and connected to a medical waste collection unit 2. As shown in FIG. 23, the device 10 has the discharge port 14 end of the manifold assembly 10 inserted into an inlet fitting 3 on the top of the unit 2. The cover 25 covering the discharge port 14 is first removed and unattached from the discharge port 14 end so that the device 10 can slip conveniently and securely into the inlet fitting 3 of the mechanism 2. As illustrated in FIG. 24, the device 10 when inserted fully is positioned vertically in a very stable and erect manner resting on the plurality of ribs 15. As shown in FIG. 23, the two vacuum inlet ports 12A and 12B are shown exposed with inlet port covers 21 and 22 removed. In FIG. 24, the inlet ports are then connected with two clear vacuum tube lines 4 as illustrated. These vacuum tube lines 4 provide suction at the surgical wound site and as illustrated in FIG. 25 when the collection waste unit 2 is turned on a vacuum pump draws vacuum through these suction lines 4 wherein the waste collection products 1 from the surgical site can be suctioned off and drained into the improved manifold assembly 10. As illustrated in FIG. 25, the waste collection products 1 from a surgical wound site can include debris 5 and the fluids 6. The vacuum hoses 4 can be maneuvered to facilitate suctioning these waste products 1 from the wound site to facilitate the surgeon's ability to observe and to surgically repair whatever he is working on without being obstructed by the debris 5 created during the surgical procedure. The debris 5 as defined herein can mean the particulate of the waste products 1 including bone chips, tissue, muscle, cartilage and blood clots in a solid or semi-solid form; whereas the fluids 6 as used herein will mean the liquid waste including wound irrigation fluids, blood and non-solid flowable matter. It is the combination of these components both debris 5 and fluids 6 that make the waste collection products 1 that must be removed. The solids or debris 5 separate from the fluid 6 in the manifold assembly 10 as the fluids flow in the waste collection unit 2.

As shown in FIG. 25, a unique swirling action is created by the manifold device 10 such that as the manifold assembly 10 is sucking the fluids 6 and debris 5 from the wound site through the inlet ports 12A and 12B they are discharged into a chamber 11 within the housing 13 along the chamber's inner wall 13A in a swirling fashion. This suction creates a substantial vortex and the debris 5 and fluids 6 flow spirally downwardly along the inner wall 13A of the chamber 11 where they are ultimately drawn into a strainer assembly 80 held in the bottom of the chamber 11 that is open to the discharge port 14 through a central opening 93. All the solid or semi-solid debris 5 particulates in the waste collection products 1 are captured in the strainer 80 in such a fashion that they are held and separated from the fluids 6 which flow directly into the collection unit 2. This can be visually observed as the housing 13 is translucent or transparent as a result, when one is operating the improved manifold device 10, they can see the debris 5 being collected along the periphery. As the debris 5 fills the strainer 80, the device 10 is always open to the central opening 93 such that it cannot be blocked or occluded. This is a significant advantage over the prior art manifold devices with filtration systems which inherently clog and block. This clogging and blocking has resulted in occurrences of reverse flow. Flow blockages are virtually impossible with the strainer 80 because the central discharge opening 93 and the discharge port 14 are always open regardless of the amount of debris 5 within the chamber 1 of the manifold housing 13.

Figure 1:
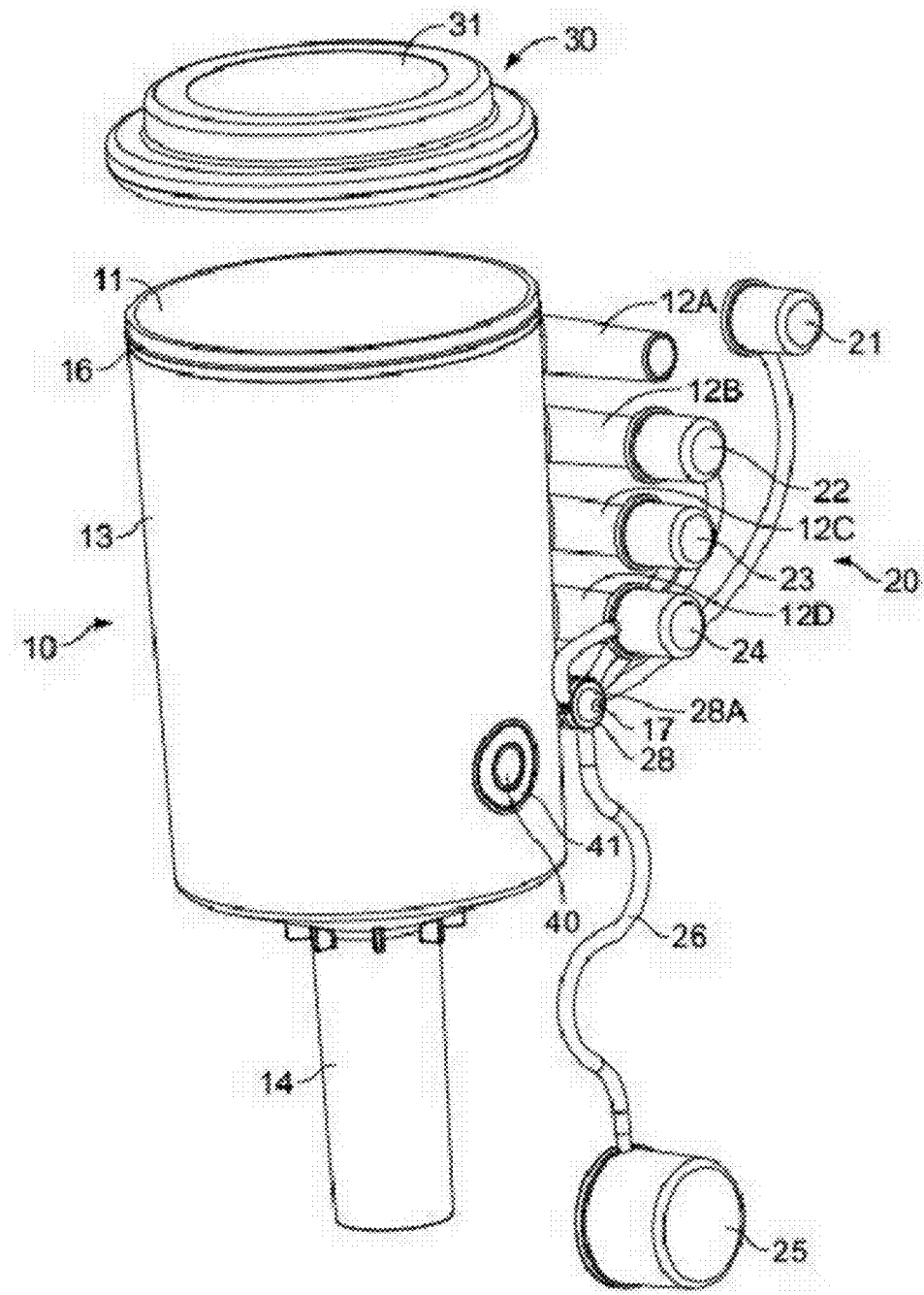
FIG. 1 is a perspective view of the multi-port manifold of the present invention with the end cap removed, one inlet port cover removed from the inlet port, three covers positioned on the inlet and the outlet discharge port open and the outlet cover shown not attached.

With reference to FIG. 1, the improved manifold assembly 10 is illustrated in a perspective view with the end cap 30 shown above and not yet attached to the housing 13. In this view the end cap 30 being removed allows one to observe the inner chamber 11 of the housing, the inner chamber 11 extends to the bottom of the housing 13 and is open to the discharge port 14 at the lower end of the figure. The discharge port 14 has a port cover 25 as illustrated; the port cover 25 is shown removed from the discharge port 14. On the side of the housing 13 a plurality of four inlet ports 12A, 12B, 12C, 12D are illustrated. This manifold housing 13 can be made with at least one of these inlet ports 12A, 12B, 12C or 12D which can have a vacuum line (not illustrated) attached which will extend to the surgical site and allow the waste collection products to be drawn into the chamber 11 when in use. The inlet port 12A is shown with its inlet cover 21 removed. The inlet covers 22, 23 and 24 are shown tethered and on the respective inlet ports 12B, 12C, 12D which they are covering. Each of the covers, both inlet covers 21, 22, 23, 24 and discharge covers 25 are tethered with lines 26. The lines 26 converge to a central attachment element 28 with an opening 28A, the opening 28A slides over a nipple 17 molded into the housing 13. The nipple 17 can be heat staked and melted in such a fashion that the tethered covers 21, 22, 23, 24, 25 cannot be dislodged from the manifold assembly 10. As shown the manifold housing 13 at the open upper end of the chamber 11 has a groove 16. This groove 16 is a locking means that allows the end cap 30 to be snapped onto the housing 13. The cap 30 has a complimentary locking means to insure that once the end cap 30 and housing 13 assembly is made, the end cap 30 cannot be removed from the housing 13.

As further illustrated, a prior-use indicator means 40 is provided, the prior-use indicator means 40 as shown is actually installed on the inside of the housing 13, the housing being transparent or translucent allows the indicator 40 to be visibly observed from the exterior of the manifold 10. A label 41 can be attached to the exterior of the housing 13 encircling the indicator 40 as illustrated. The label 41 provides a warning indication that when the indicator means 40 changes color, in this case from initially gray or white to red, when exposed to moisture it is an indication that the device has been previously used. This prior-use indicator means 40 is reactive with fluids, once moisture hits the indicator means 40 it irreversibly changes color from the original white or gray to a red color. The label 41 identifies and warns of this feature which allows the operating room personnel to understand that this device 10 has been previously used. This prior-use indicator means 40 is useful in that it helps the users to know when the device has been previously used. The port covers 21, 22, 23, 24 and 25 when attached allow the device 10 to avoid being exposed to moisture during shipping and transit, alternatively the device 10 is preferably placed in a vacuum sealed pouch so that it cannot be exposed to any fluid or humidity that might otherwise trigger a false positive reading on the prior-use indicator 40 regardless of the cover's attachment.

Figure 2:
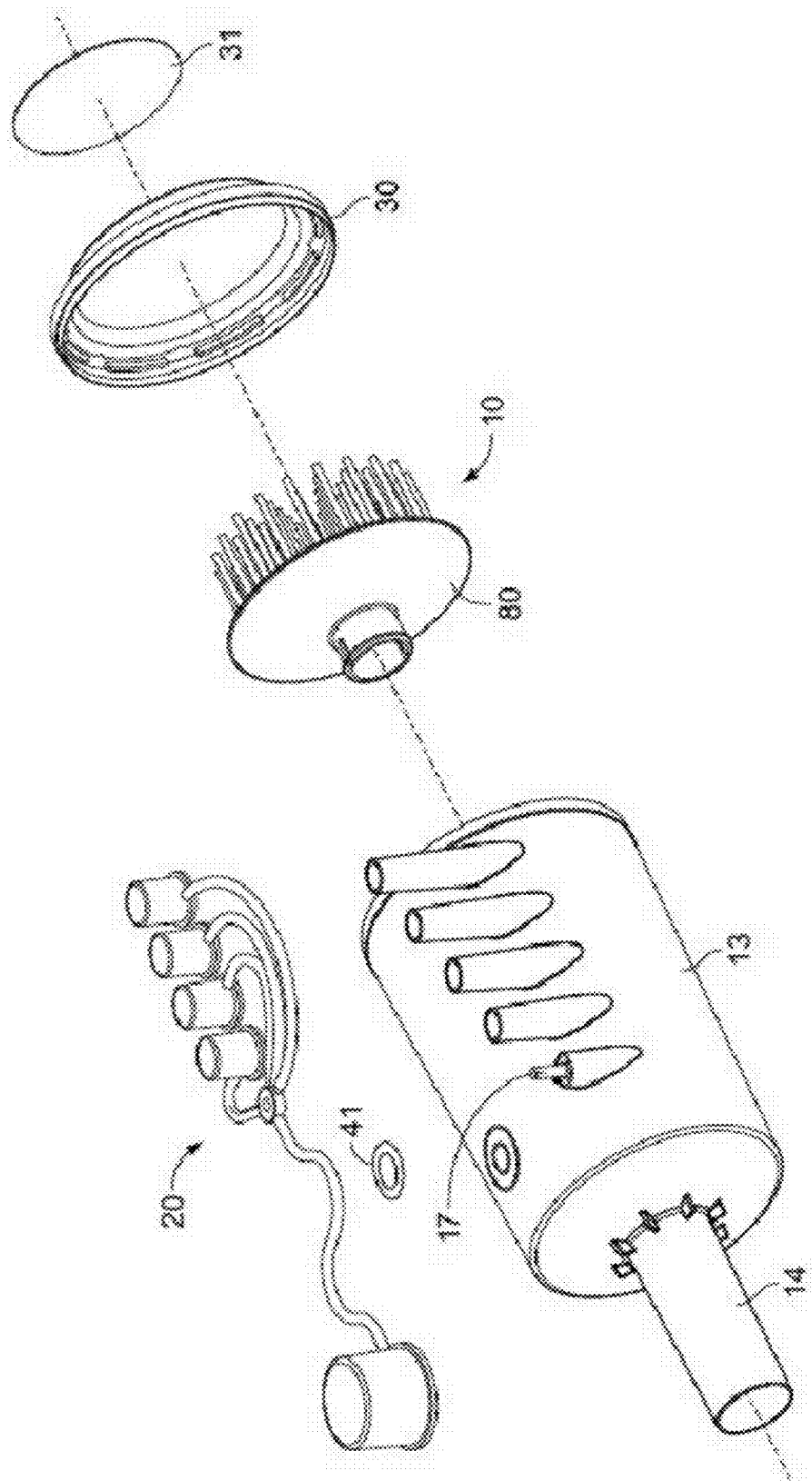
FIG. 2 is an exploded view of the multi-port device of FIG. 1.

With reference to FIG. 2, an exploded view of the entire improved manifold assembly 10 is illustrated. As shown a label 31 is shown removed from the top of the end cap 30. In between the end cap 30 and the housing 13 of the manifold is shown a strainer 80. The strainer 80 is adapted to fit inside the chamber 11 of the housing 13 and when assembled the strainer 80 is open to the cylindrical or otherwise conical shaped discharge outlet port 14. The tethered covers 20 are shown removed from the housing assembly 13, the nipple 17 is shown prior to being heat staked in this view.

Figure 3:
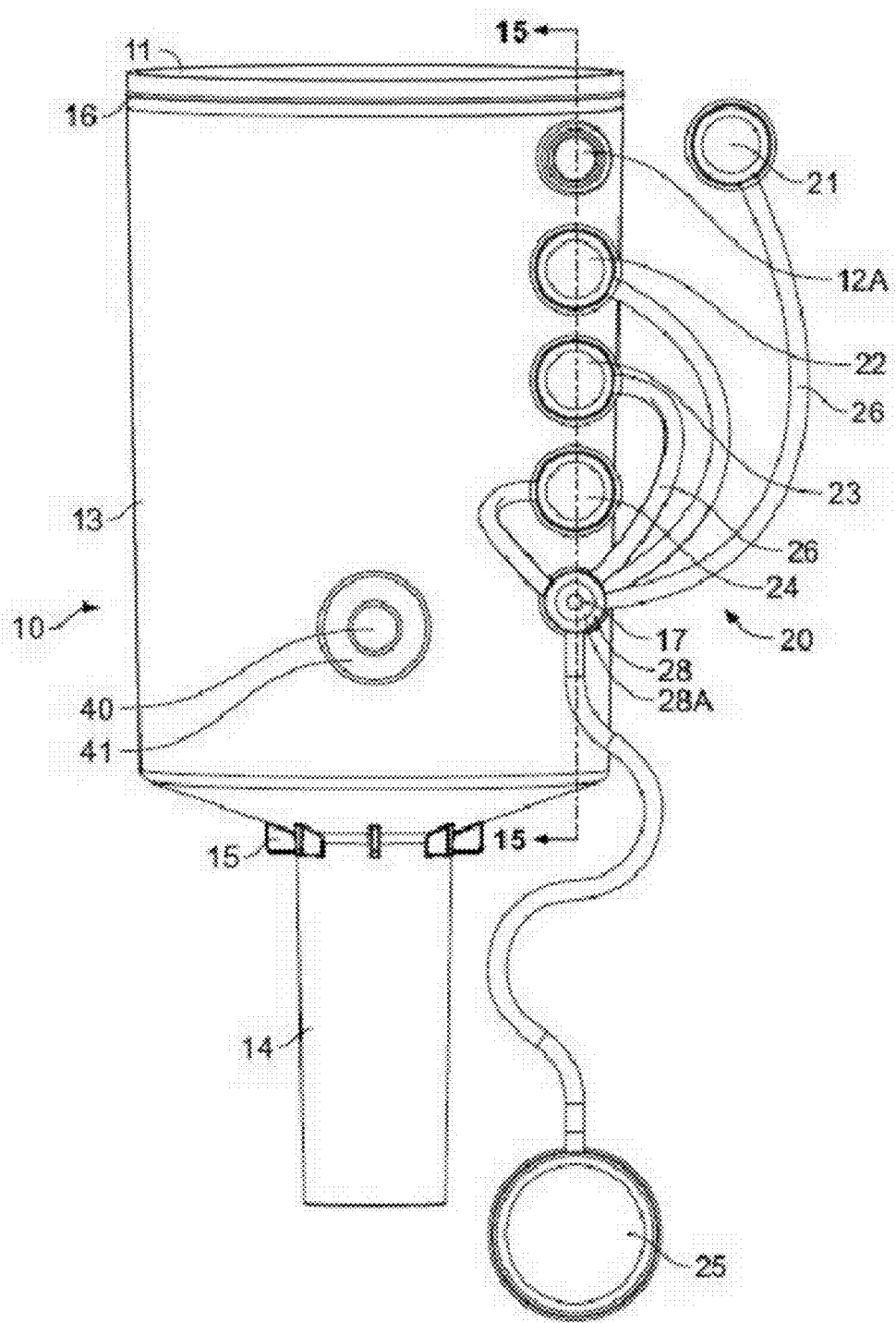
FIG. 3 is a side view of the housing with the end cap removed (not shown) and the port covers and use indicator shown.

With reference to FIG. 3, the device 10 is shown with the tethered covers 20 heat staked directly onto the housing 13 at the nipple 17 and further shows the prior-use indicator means 40. The cap 30 is not illustrated in this view. Again this view shows the locking means for snap locking the cap 30 in place which is the groove 16 that is molded into the housing 13 exterior surface. At the interface between the discharge port 14 and the bottom of the housing 13 is a plurality of ribs 15 extending like small spokes that extend radially outward from the discharge port 14. These spokes or ribs 15 provide a means to help support and stabilize the device 10 when it is inserted in the collection unit 2.

Figure 4:
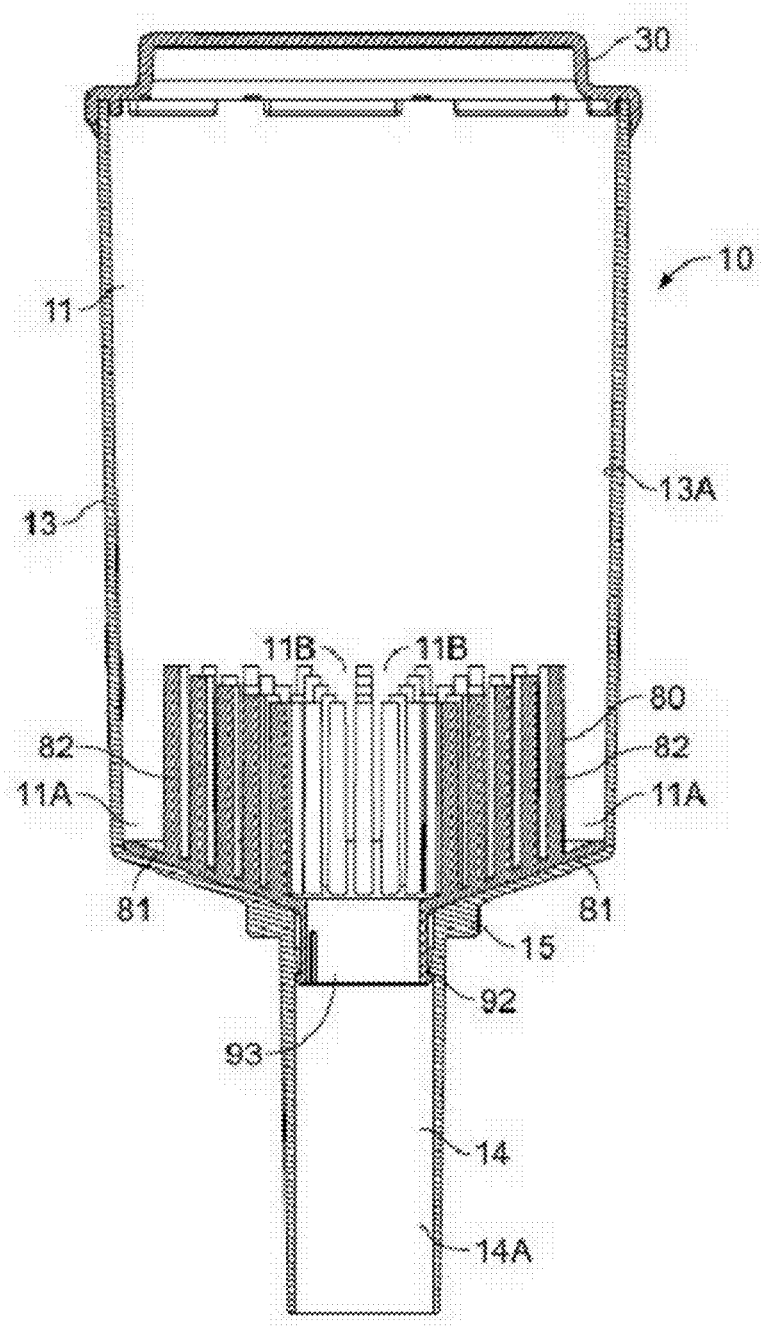
FIG. 4 is a cross sectional view of the multi-port manifold with the peg strainer installed.

With reference to FIG. 4, a cross sectional view of the improved manifold assembly 10 is shown. In this view the inner chamber 11 is illustrated, inside the inner chamber 11 is a strainer 80 that is shown open to the discharge port 14. The end cap 30 is shown snapped on and securely assembled to the end of the housing 13. As illustrated in this view a channel 11A is formed circumferentially around the plurality of radially outermost projections 82 and the inner wall 13A of the chamber 11. This space or channel 11A located between the outermost projections 82 that extend from the base 81 of the strainer 80 and the inner wall 13A provides a void volume into which the waste collection products 1 can be distributed as the waste collection products spiral around the inner surface of the wall 13A of the chamber 11 in a downward direction towards the strainer 80, the debris 5 is initially captured in this circumferentially continuous channel 11A. Once the debris 5 is captured, the flow of waste product material is directed inwardly through intersecting radially extending channels 11B toward the central opening 93 of the strainer 80, however, because the pegs 82 are positioned on radial lines or lines that extend from a closely spaced innermost grouping of projections 82 and flare out radially, these radial channels 11B are widest at the intersection with the channel 11A between adjacent rows of pegs 82 narrow as they extend radially inwardly and as they narrow can provide increased straining of the debris 5 and prevent it from entering into the discharge channel 14A and thereby prevent the debris 5 from entering into the collection unit 2.

Figure 5:
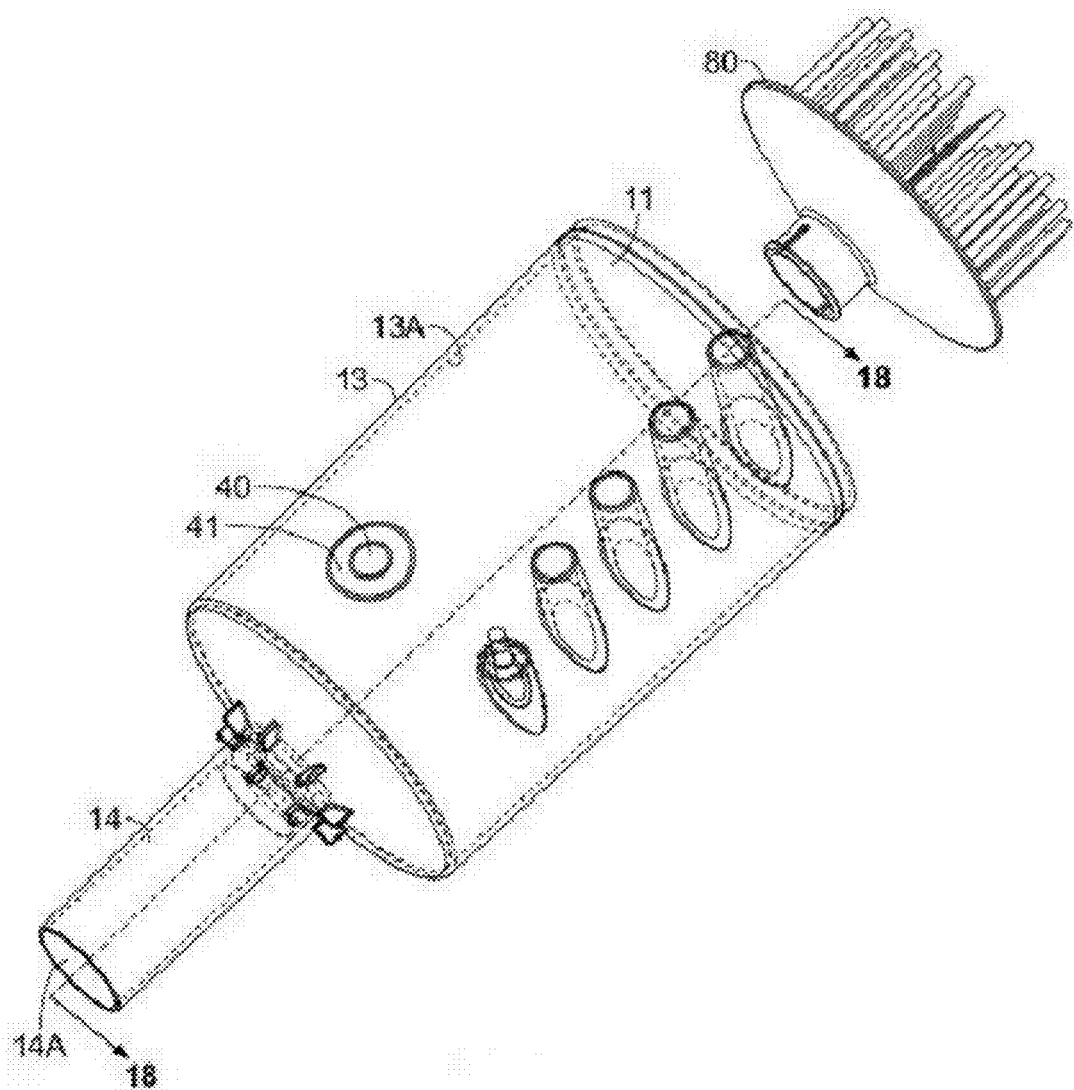
FIG. 5 is a tilted perspective view of the manifold housing and the peg strainer illustrating how they are assembled.
Figure 6:
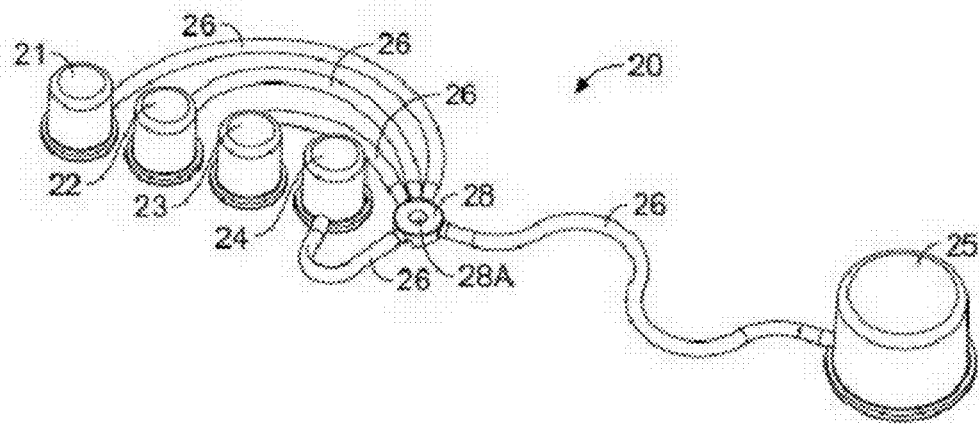
FIG. 6 is a perspective view of the port cover assembly.
Figure 7:
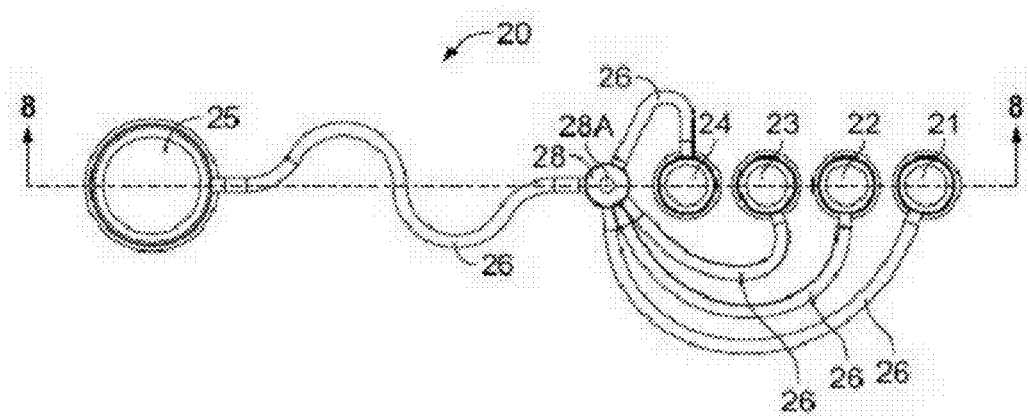
FIG. 7 is a top plan view of the port cover assembly.
Figure 8:
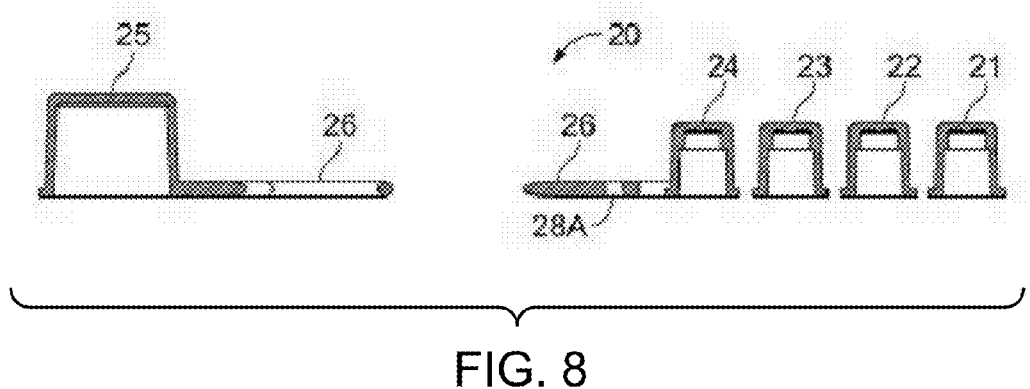
FIG. 8 is a cross sectional view of the port cover assembly taken along lines 8-8 of FIG. 7.
Figure 9:
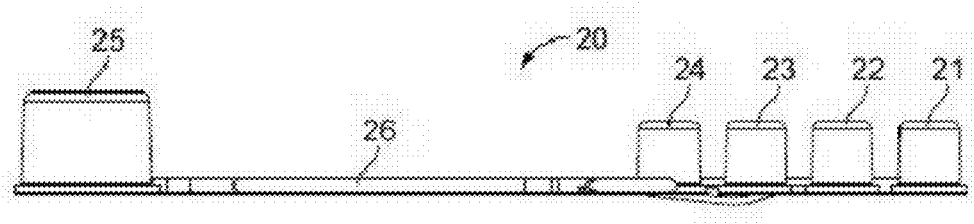
FIG. 9 is side plan view of the port cover assembly.
Figure 10:
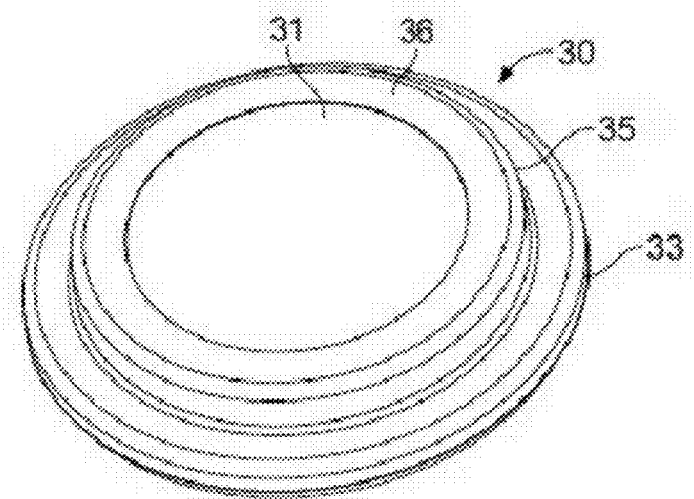
FIG. 10 is a perspective view of the outside of the end cap.
Figure 11:
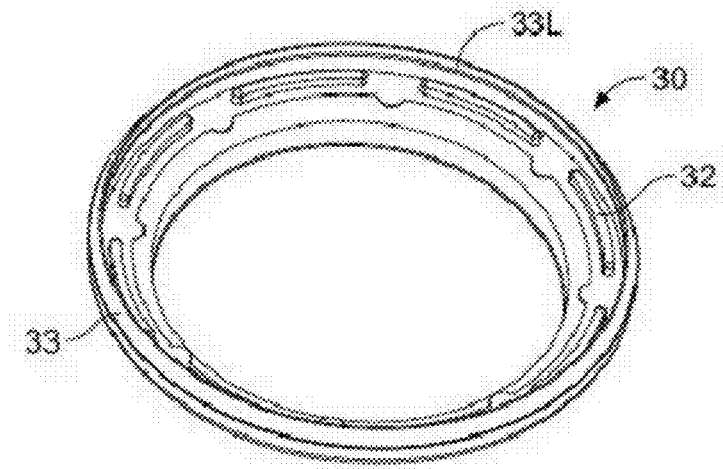
FIG. 11 is a perspective view of the inside of the end cap.
Figure 12:
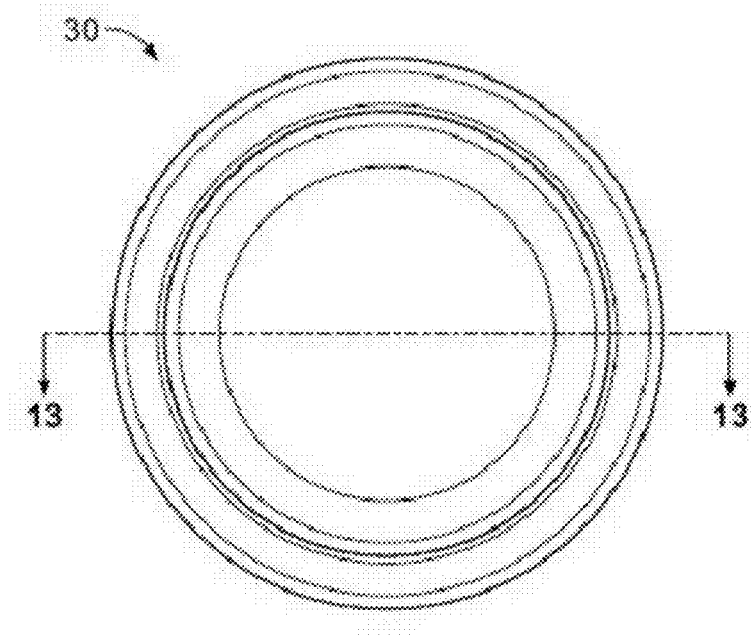
FIG. 12 is a top plan view of the end cap.
Figure 13:
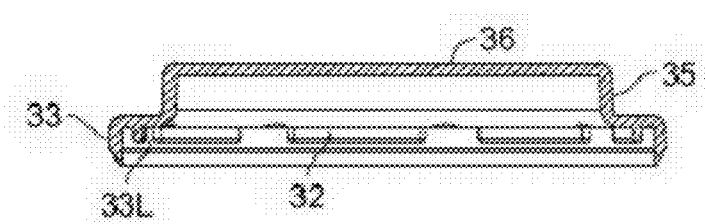
FIG. 13 is a cross sectional view of the end cap taken along lines 13-13 of FIG. 12.
Figure 14:
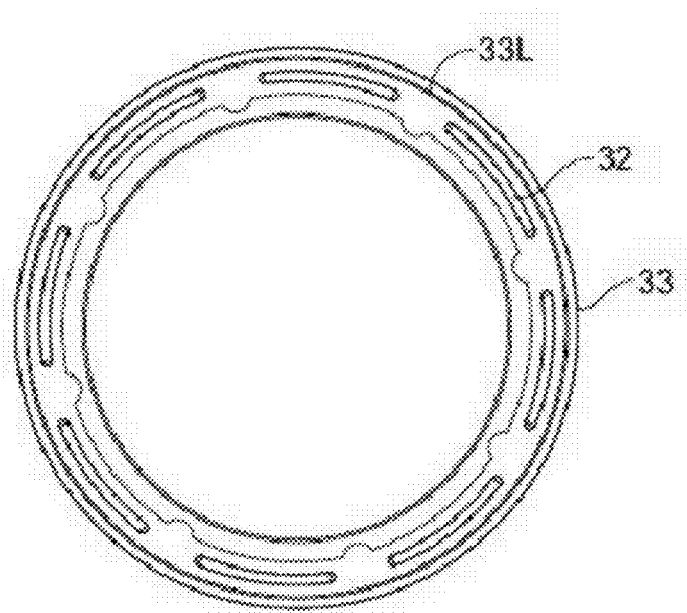
FIG. 14 is a bottom or inside plan view of the end cap.

In FIG. 5 a perspective is shown where the housing 13 interior is shown in dashed lines. The housing 13 is on a tilted view and the strainer 80 is shown above the housing 13 as illustrated. The manifold housing 13 in this view illustrates how the inlet ports 12A-12D enter into the chamber 11 in a manner in which the internal openings of the inlet ports 12A-12D terminates at ends that are somewhat oval in shape and flush to the inner wall 13A of the chamber 11. This ability to provide the inlet ports 12A-12D in such a fashion enables the device 10 to have virtually no inner wall obstructions that would impede the downward spiral flow of the waste collection products 1 coming from the patient with the fluids 6 being transferred to the collection unit and the debris 5 being captured in the strainer 80.

With reference to FIGS. 6-9, the tethered cover assembly 20 is illustrated. As shown, the cover assembly 20 has a plurality of inlet port covers 21, 22, 23, 24 and discharge port cover 25 all tethered by lines 26. These lines 26 maintain the covers 21, 22, 23, 24 and 25 in an assembly 20 which converge to an attachment location 28 with a central hole 28A, this central hole 28A is to be positioned over a nipple 17 on the housing 13 when assembled. When so positioned the nipple 17 can be heat staked which will weld around the central location 28 securing it firmly to the housing 13. This cover assembly 20, when used, allow the device 10 to be sealed at all inlet port openings 12A-12D and the discharge port 14 opening 14A. This facilitates removal of the used device 10 sealing all openings so that the biological material in the manifold 10 can be safely discarded.

With reference to FIGS. 10-14, the end cap 30 is illustrated. The end cap 30 provides a unique closure assembly that includes top 36 onto which a label 31 can be affixed and an outer flange portion 33 of a diameter sufficiently large to fit over the housing 13. As shown a lip ring 33L is provided as a locking means that projects radially inwardly from the flange 33, this lip ring 33L complimentarily fits into a locking means which is the groove 16 on the housing 13. Once assembled, the interlocking groove 16 and lip ring 33L secure the cap 30 in such a fashion that it is no longer removable from the housing 13 without damaging or otherwise disabling the end cap 30. Interior of the flange 33 is shown a plurality of arcuate segments projecting as arcuate ribs 32, these ribs 32 are spaced a distance sufficient that the wall 13A of the housing 13 can be inserted between flange 33 and arcuate ribs 32. The projections 32 lie radially inward and adjacent to the interior housing wall 13A in the chamber 11. On assembly, when the end cap 30 is snapped onto the housing 13 the locking feature 33L interlocks with the groove 16 and simultaneously the ribs arcuate 32 are entered into the chamber 11 and provide radial supports for the end of the manifold housing 13. These arcuate ribs 32 secured onto the housing 13 will prevent the housing 13 from collapsing under vacuum pressure and provide a rigid support. This is important because under severe vacuum, some manifold chambers have been known to collapse, it is virtually impossible for the improved manifold assembly 10 of the present invention to collapse, at least at the ends where the end cap 30 and discharge port 14 are provided because stiffening features such as the end cap 30 with arcuate segments 32 and the discharge port with ribs 15 would prevent any such occurrence. This is valuable in that the housing 13 itself can be made lighter than most conventional manifolds.

Figure 15:
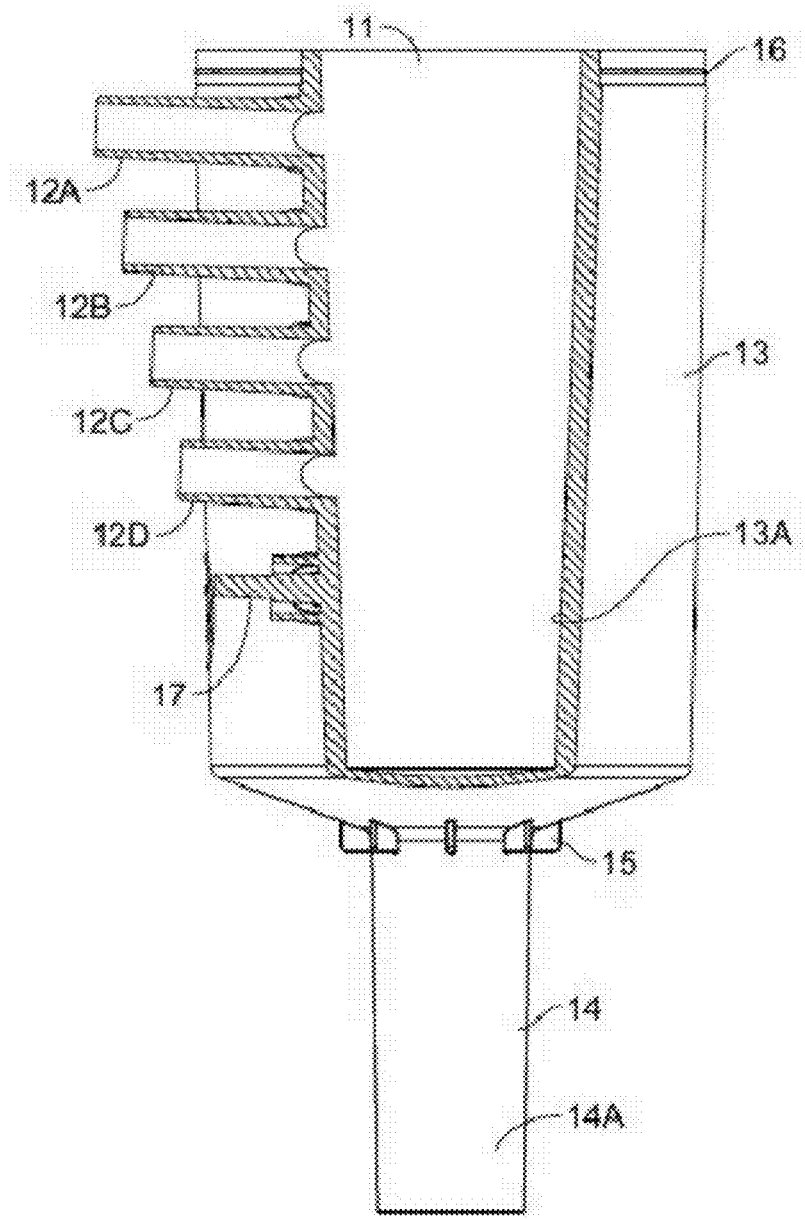
FIG. 15 is a cross sectional view of the housing showing a cut away looking into the debris chamber taken along lines 15-15 of FIG. 3. The port covers not shown.
Figure 16:
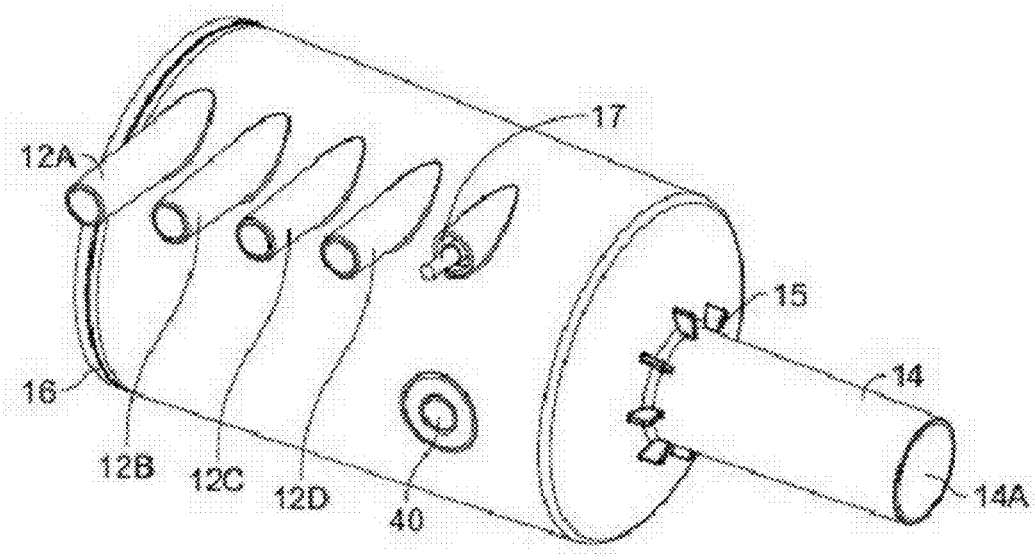
FIG. 16 is a perspective view of the manifold housing showing the outlet discharge port end.
Figure 17:
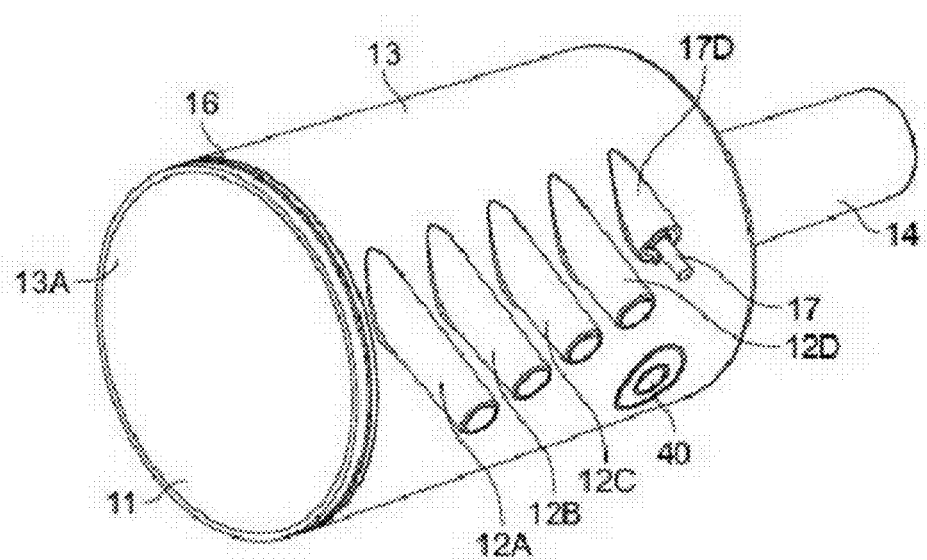
FIG. 17 is an opposite perspective view of the manifold housing showing inside open end into debris chamber.
Figure 18:
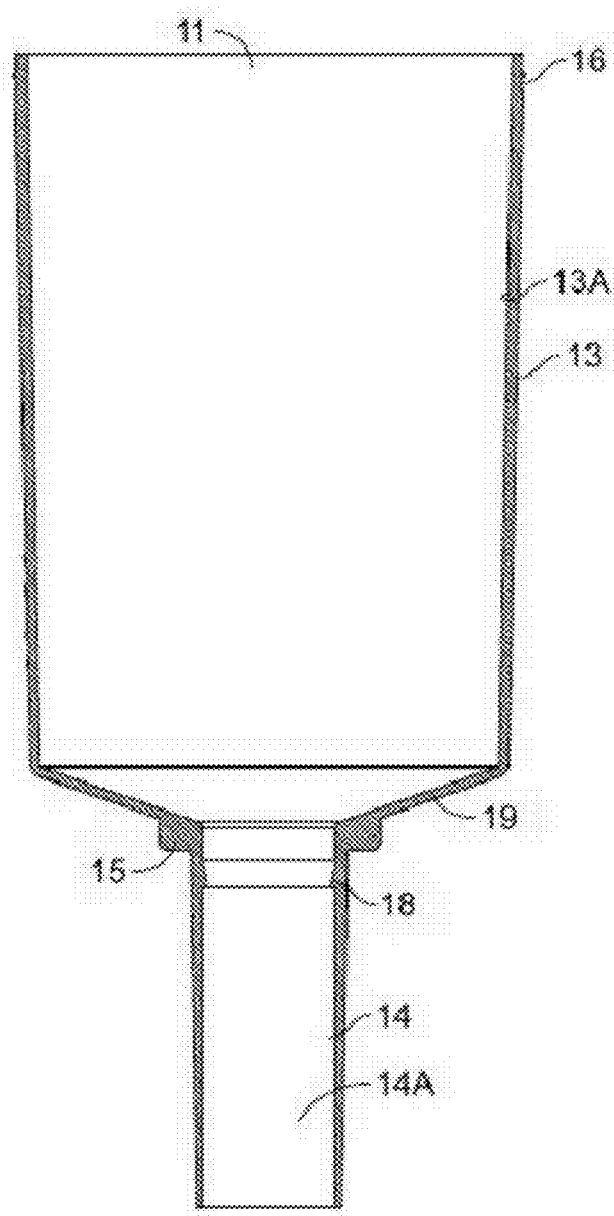
FIG. 18 is a cross sectional view of the manifold housing taken along lines 18-18 of FIG. 5.

With reference to FIGS. 15-18, the manifold housing 13 is further illustrated. In FIG. 15, a clear demonstration of the inlet ports 12A-12D is observable when cut in cross section. This view and FIG. 5 enables one to see how the inlet ports 12A-12D are aligned adjacent the wall 13A of the chamber 11 in such a fashion that the interior ends are flush and tangent to the wall 13A as they terminate in the chamber 11. This offset and vertical stacking of the inlet ports 12A-12D enables the device 10 to be made in a rather efficient manner. As shown in FIGS. 15, 16 and 17, the inlet port is longest at 12A and progressively shorter as they lower down to port 12D, the nipple feature 17 is also inward of the ends of the inlet ports 12A-12D. This ensures that the inlet ports 12A-12D are readily exposed for assembly to vacuum lines 4 when in use and provides an easy way of attaching lines while still being able to get ones hands around the vacuum tube and access the inlet port ends. In the preferred embodiment, each inlet port 12A-12D is tilted off horizontal by an amount equal to 3 degrees or more. This enables the opening of each inlet port to direct the flowing waste collection material in a path along the interior wall 13A in a downward spiral or swirl as it exits the flush interior end of the inlet ports 12A-12D. This greatly facilitates the initial capture of debris 5 in the circumferentially continuous channel 11A where it subsequently can be captured in the narrowing radial channels 11B of the strainer assembly 80. This flow path directed by this unique positioning of the inlet ports 12A-12D enables a vortex effect or swirl to ensure the debris 5 is effectively trapped in the peg strainer assembly 80.

Figure 19:
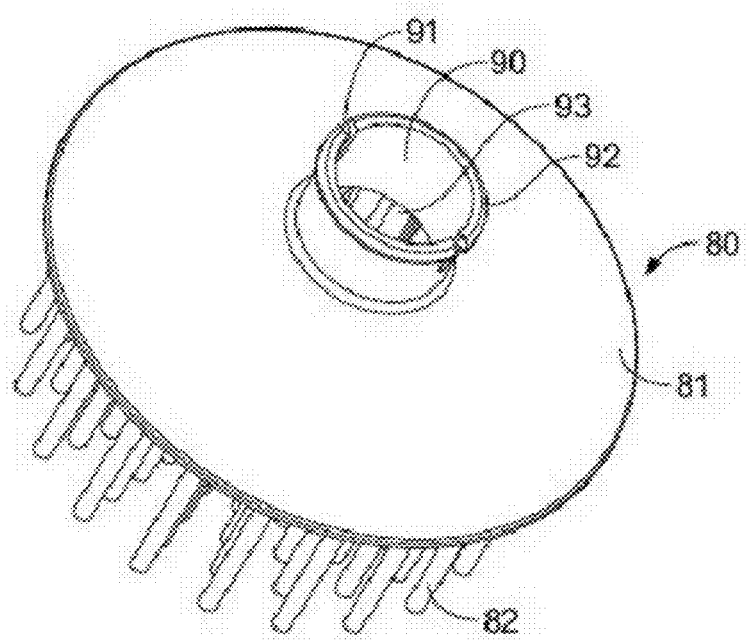
FIG. 19 is a perspective view of the peg strainer assembly bottom or base side exposing the cylindrical locking attachment for securing the peg strainer to the housing.
Figure 20:
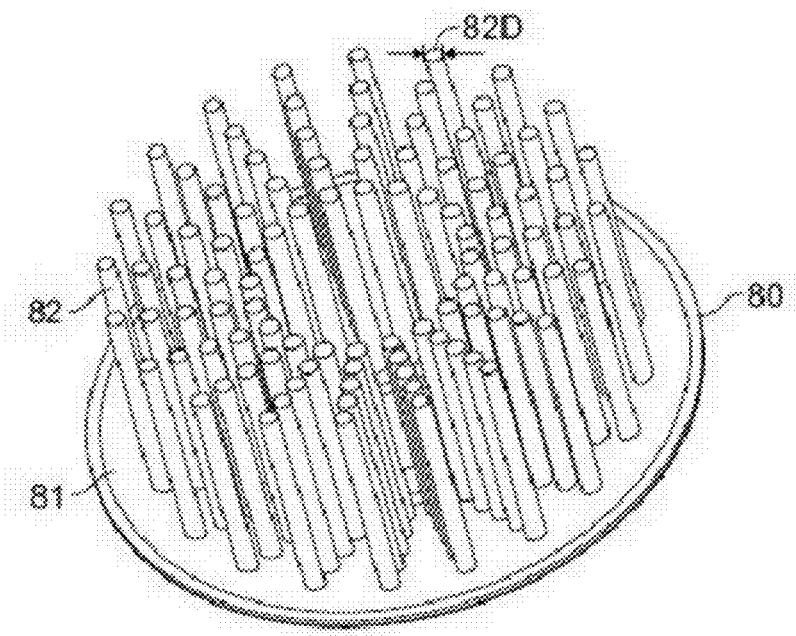
FIG. 20 is an opposite perspective view of the peg strainer assembly.
Figure 21:
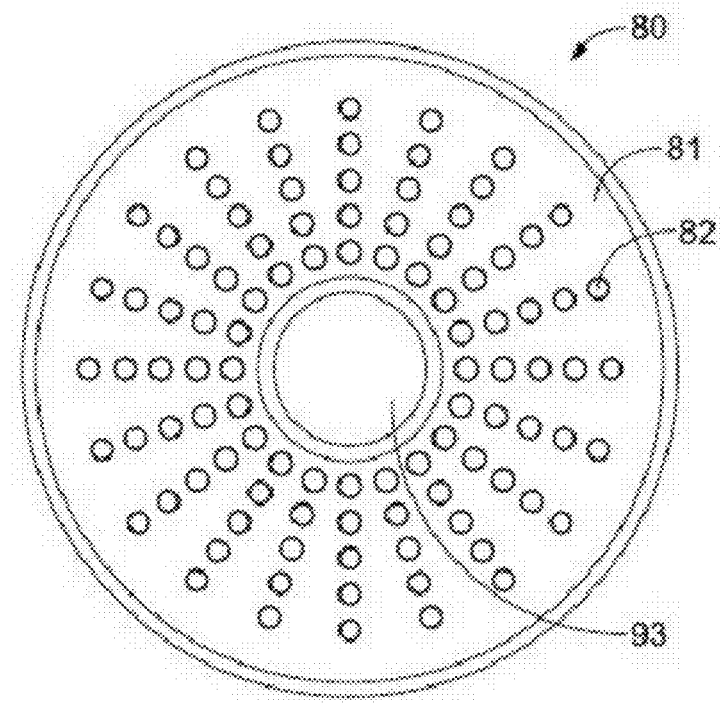
FIG. 21 is a top plan view of the strainer.
Figure 22:
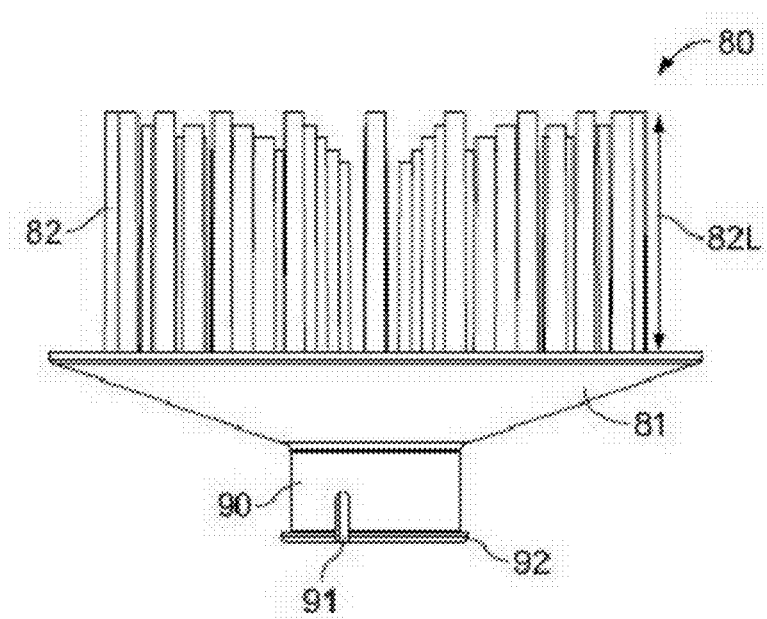
FIG. 22 is a side plan view of the strainer.

With reference to FIGS. 19-22, a strainer assembly 80 is shown. As shown, the strainer assembly 80 has a plurality of projections 82 extending from the base 81 of the strainer 80 vertically outward upon assembly. These vertically extending projections 82 can be in the form of round pegs 82 as illustrated. Alternatively, the round shapes could be triangular, oval or any shape as long as the cross sectional shape of each peg 82 is sufficient to provide enough rigidity so that the strainer projections or pegs 82 do not bend or collapse during normal use of debris collection. As shown, the base 81 is conically shaped and adapted to fit in the conical end 19 of the housing 13 above the discharge port 14 and extends down to a cylindrical connection port 90, the cylindrical connection port 90 has a central opening 93, the central opening 93 as shown in FIGS. 19 and 21 allows the waste fluids 6 to transfer through the strainer 80 and into the discharge opening 14A of the discharge port 14. As shown, the cylindrical end 90 has a projecting rib 92 which complimentarily fits into an internal rib 18 on the collection housing 13 shown in FIG. 18. The rib 92 has slits or cutouts 91 illustrated which allow this cylindrical portion 90 to flex slightly on assembly. Once the strainer 80 is jammed into the housing 13 the complimentary rib 92 interlocks with the internal rib 18 on the interior opening 14A of the discharge port 14 of the housing 13. This is as illustrated in FIG. 4. As shown in FIG. 21, the projections 82 are all aligned in rows extending in a radial direction, the innermost row being most closely spaced because it is of the smallest diameter wherein the outermost row of peg projections 82 are more widely spaced due to the increasing diameter of the strainer 80. The peg projections 82 are aligned in lines of rows of five peg projections 82 each, more or less peg projections 82 can be used, the important feature is that the projections 82 independently extend from the base 81 and are therefore positioned so that fluids 6 are able to allow flow in any direction around the peg projections 82. As shown, the peg projections 82 are round pegs. As further shown, the peg projections 82 are of a preferred or predetermined length 82L. The length 82L of the peg projections 82 in combination with the diameter 82D of the pegs 82 defines the stiffness or the amount of flexure of the peg. By providing a sufficiently long peg projection 82, a large amount of debris 5 can be collected in the strainer 80. Additionally, and quite beneficially, the strainer 80 with peg projections 82 being of the length 82L as illustrated which is approximately one to two inches in length and having a diameter 82D in the range of greater than $\frac{1}{8}^{th}$ of an inch to less than ¼ inch the strainer 80 is able to provide sufficient rigidity of the pegs 82 while the peg spacing allows large volumetric voids of the radially extending flow channels 11B and openings between pegs through which the fluid can pass, but the debris 5 particulate matter cannot. As illustrated in FIG. 25, there is a continuous void volume in channel 11A created between the pegs 82 and the inner wall 13A of the housing 13, this inner wall 13A of the housing 13 enables the device 10 to create a circumferentially continuous flow channel 11A that will allow the fluids 6 as they swirl along the inner side of the chamber 11 to be directed into this opening or channel 11A and then radially moved toward the center of the strainer 80, however, due to the narrowing of the radially extending openings or channels 11B between adjacent rows of pegs 82, the debris 5 is captured and therefore kept from entering into the collection unit 2.

As previously illustrated, the manifold housing 13 is shown with a generally circular cross section for molding purposes, it is actually conically tapered slightly to allow the manifold housing 13 to release from a mold when it is injection molded. All of the components, with the exception of the port covers, illustrated in the device 10 are made out of a plastic, preferably polypropylene, this polypropylene material as shown enables the housing 13 to be made translucent. The housing 13 being translucent enables the user to visually observe the debris as it is swirling in a vortex around the interior of the chamber 11. The strainer 80 in the preferred embodiment and the end cap 30 are made in a complimentary blue color, any other color is equally acceptable. The port cover assembly 20 is made of an elastomeric material of a soft rubber like synthetic or natural material. The prior-use indicator means 40 when assembled into the housing 13 is positioned internally aligned with an exterior optional boss in one location on the device housing 13, as shown in FIG. 5, this is generally 90 degrees from the inlet ports 12A-12D. The indicator means 40 is an indicator activated when the device 10 has been exposed to liquids. These indicators 40 have been made to be fixed onto the chamber 11 using an adhesive on a frontal surface of the indicator to secure the indicator means 40 to the chamber 11. Once secured, the indicator 40 is permanent and will maintain its original color until it is activated by exposure to moisture. These and other features of the device 10 are as illustrated, as previously mentioned, the improved manifold device 10 can be made with a single manifold inlet port 12A allowing one vacuum line 4 to be used or preferably, as shown in the best mode, with four vertically stacked inlet ports 12A-12D to allow as many as four vacuum lines 4 to be attached to a single manifold assembly 10. As further described, this device 10 is uniquely set for a one time use, it is virtually impossible without damage to remove the end cap 30 from the housing 13. The housing 13 is also clear and evident to any user whether the device 10 has been previously used by the red indicator 40 and warning label 41 on the device 10. These features greatly enhance the safety of the device 10, more importantly, the device 10 as shown has no fine mesh filters as in previous prior art devices. It has been found that these prior art filters are essentially the primary reasons why manifold devices clog because of the trapping of the high viscosity blood and other fluids prevent the device from filling properly and prevent the device from collecting all the debris it should. In alternative devices, when this occurs there is an overflow or a bypass as shown in the prior art patent previously discussed. This is a solution that ensures that byproducts will enter into the waste collection system during a blockage, this is generally considered a non-acceptable practice in a manifold device. It is preferred that the debris 5 be held in the manifold and not allowed to flow over a bypass device. Once the device is full, even if it is used by a single patient, it is recommended that it be removed and replaced with a new device. The prior art recommends just allowing the debris to overflow in a bypass way. The present invention device 10 can capture more material without the use of any clogging type filtration and generally cannot clog because the strainer 80 central opening 93 feeding the discharge opening 14A is such that no matter what size debris 5 or material gets into the assembly, the strainer 80 prevents it from blocking flow path channels 11A and 11B therefore vacuum is never lost using the present invention. These and other features can be found in the claims.

Figure 26:
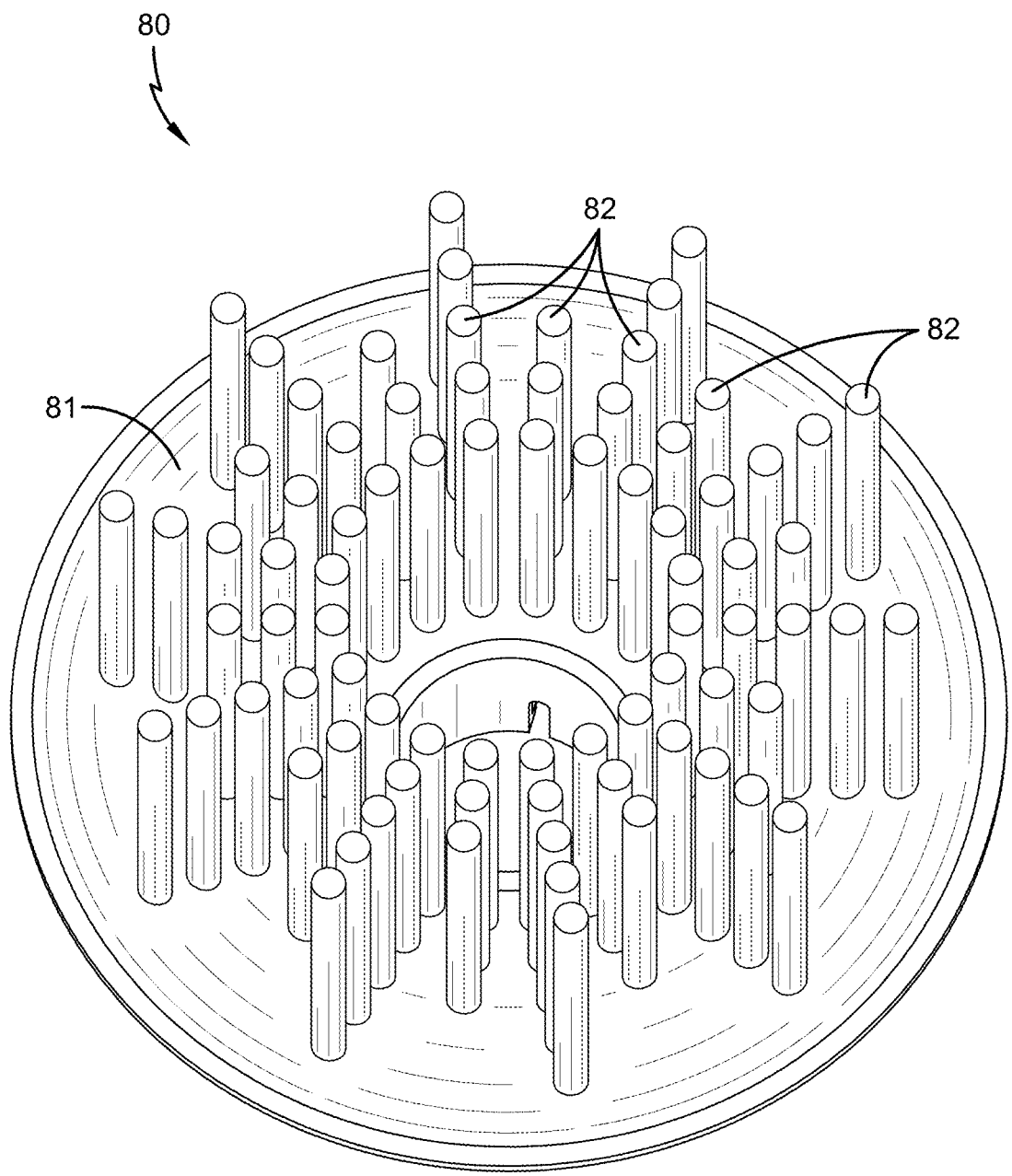
FIG. 26 shows an alternative embodiment peg strainer.

With reference to FIG. 26, an improved peg strainer 80 is illustrated. Projecting upward from the base 81 are radially positioned pegs 82. A plurality of first rows of pegs 82 has each first row five pegs 82 extending outwardly from a center peg 82 adjacent the central opening 93. A plurality of second rows has each second row having three pegs 82 extending outwardly from a center peg 82 adjacent the central opening 93. The strainer 80 has the plurality of first rows spaced by an adjacent second row. In this configuration, the gap between the manifold housing and the outermost peg 82 is varied, the first rows being closer than the second rows to the housing wall to form larger channel inlets to trap debris between the strainer 80 and the housing and to channel fluids to the central opening 93.

Figure 27:
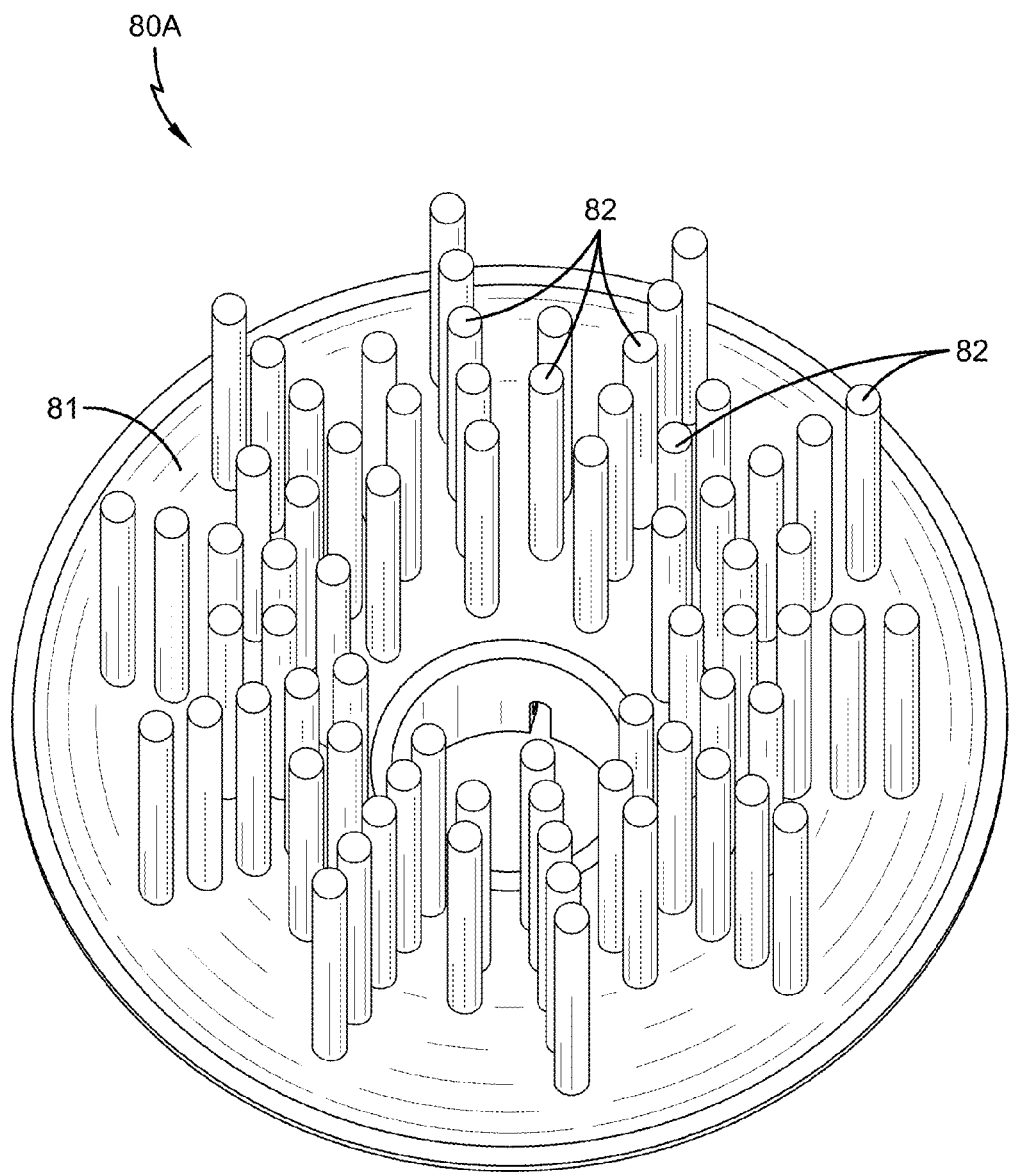
FIG. 27 shows another alternative embodiment peg strainer.
Figure 28:
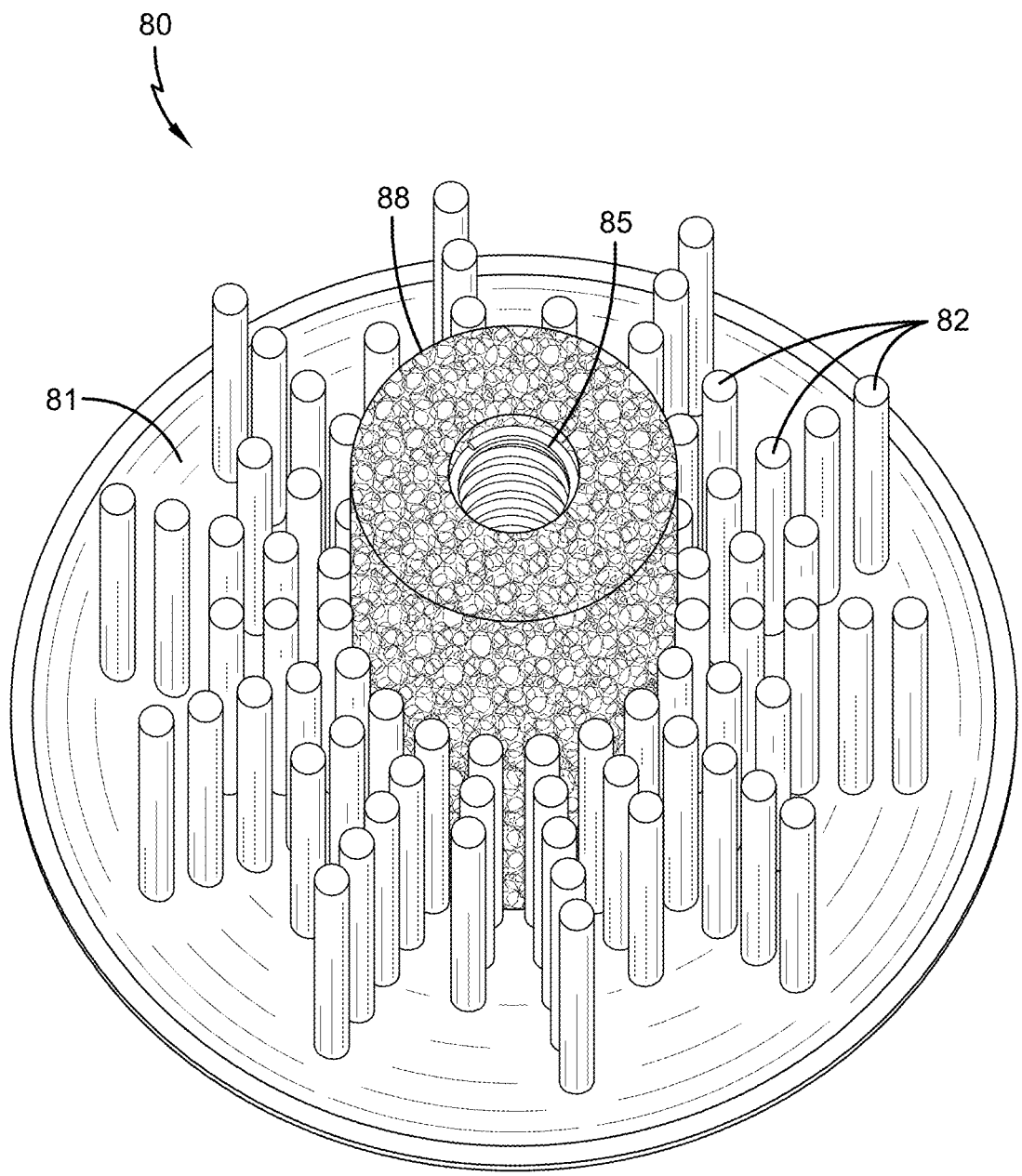
FIG. 28 shows another alternative embodiment peg strainer assembly with a central reinforced debris screen.
Figure 29:
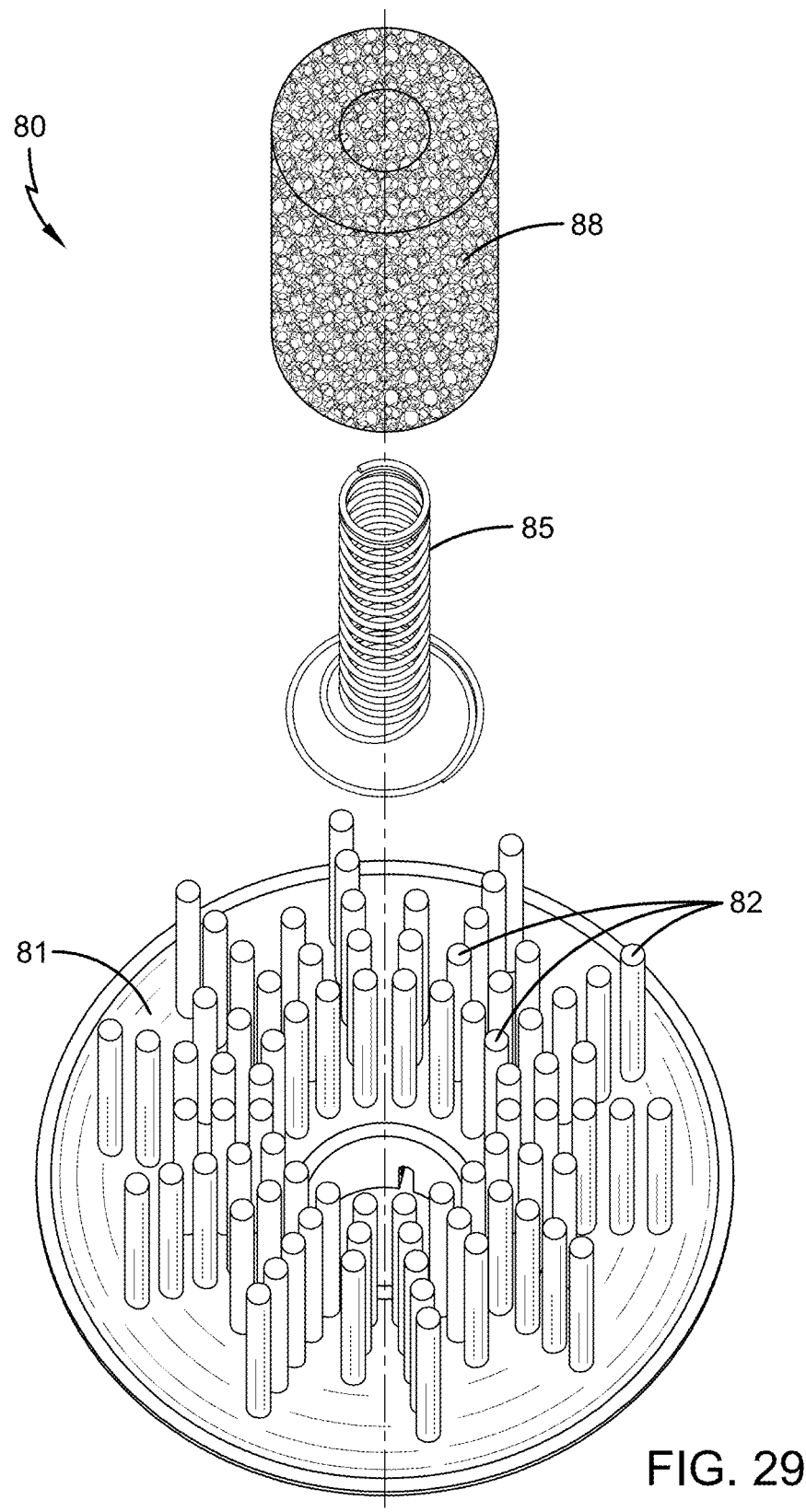
FIG. 29 is an exploded view of the peg strainer assembly of FIG. 28.
Figure 30:
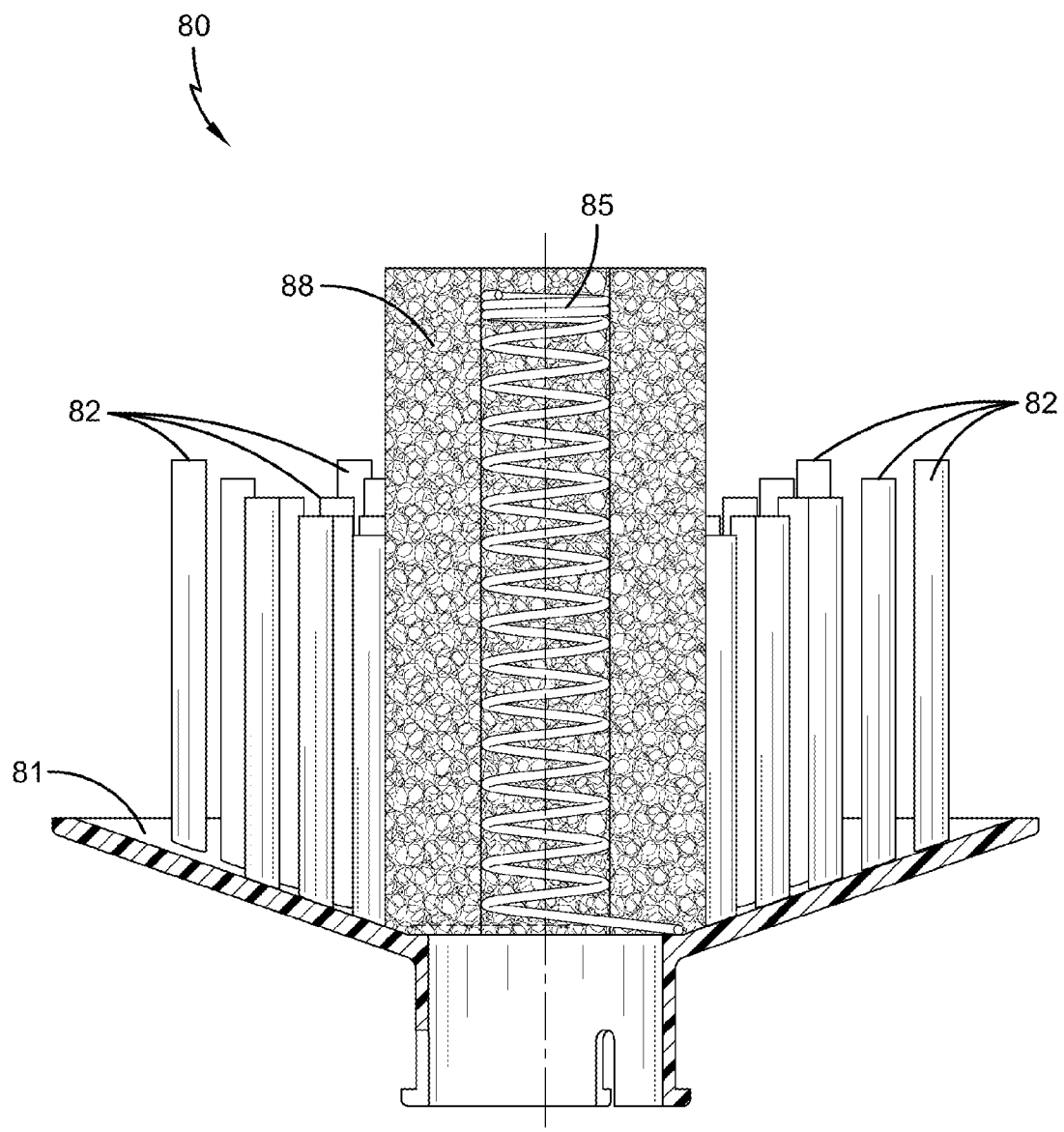
FIG. 30 is a cross-sectional view of the peg strainer assembly of FIG. 28.

In FIG. 27, another strainer 80A is illustrated showing the pegs 82 of the second row having only two pegs. In this embodiment, the innermost center peg 82 of the second row is positioned outward of the innermost center peg 82 of the first row. This is an optional feature on the strainer 80A that can be used in place of strainer 80 if desired, as shown in FIGS. 28, 29 and 30. The peg strainer 80 is shown that facilitates the positioning of a debris blocking tubular cylindrical mesh type net 88 reinforced by a coiled reinforcing member or spring 85 configured to prevent the debris blocking net 88 from collapsing under suction vacuum. The spring 85 has an enlarged end that rests on a groove in the base 81 near and adjacent the central opening, as shown in FIGS. 29 and 30. As shown, the net 88 can be glued or otherwise welded or adhesively affixed to the strainer 80 along the base 81 and/or the inner or center pegs 82 while leaving the central opening 93 clear. In this embodiment, the net 88 has a height substantially higher than the pegs 82, about 1.5 times or more the length of the pegs 82, preferably about 2 times or more. This means that debris moving above the tops of the pegs 82 is efficiently blocked from entering the central opening 93. This debris blockage, while impeding solid debris, has no effect on fluid flow due to the large unrestricted mesh openings of the net 88 and the large center opening maintained open the coiled reinforcing member 85. This feature provides the flow benefits of the earlier strainer 80, but with enhanced debris blocking and entrapment capacity. As illustrated, the hollow cylindrical net 88 is a very open celled mesh like structure for maximum fluid flow through the net 88 exterior into the interior and down the reinforced central opening out the center opening 93. In this embodiment virtually all solid debris is entrapped inside the housing.

As shown, large accumulations of tissue and bone fragments can be strained and held in the housing virtually filling it if so desired by the use of the net 88 reinforced by the member or spring 85. As shown, the net 88 is made of a synthetic plastic material and the member 85 is made of spring steel plated or coated or stainless steel.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A waste collection manifold assembly comprises:
   a housing having at least one inlet port for receiving waste collection products through a vacuum line, the housing having an interior chamber for receiving the waste collection products and a fluid discharge port for passing fluids into a waste collection unit;

a strainer, the strainer being located in the interior chamber and above the fluid discharge port;

wherein the at least one inlet port is positioned to open alongside an interior chamber wall of the housing above the strainer to direct a flow of the waste collection products in a downward swirl along the interior chamber wall toward the strainer;

wherein the strainer has a plurality of upwardly extending peg projections extending from a conically shaped base with a center opening; and wherein the upwardly extending peg projections are aligned in a plurality of first and second radial rows extending from the center opening toward the interior chamber wall, the upwardly extending peg projections of the first radial rows extending outwardly from the center opening further than the upwardly extending peg projections of the second radial rows.

2. The waste collection manifold assembly of claim 1 further comprises:

a non-removable end cap with a locking means for attachment to the housing; and wherein the housing has an open chamber end with a complimentary locking means for accepting the non-removable end cap for making a permanent attachment to seal the open chamber end.

3. The waste collection manifold assembly of claim 2 wherein the complimentary locking means of the non-removable end cap is a projecting ring and the complimentary locking means of the housing is a complimentary groove each having mating surfaces inclined to snap locking together on assembly.

4. The waste collection manifold assembly of claim 3 wherein the non-removable end cap further comprises a plurality of arcuate stiffening ribs projecting downwardly from the non-removable end cap, each arcuate stiffening rib being spaced from the complimentary locking means of the housing a distance sufficient to position the interior chamber wall of the housing between the arcuate stiffening ribs and the complimentary locking means of the non-removable end cap, the arcuate stiffening ribs preventing the interior chamber wall of the housing from collapsing under vacuum.

5. The waste collection manifold assembly of claim 1 wherein the housing has a circular shape when viewed in cross section in a portion of the housing aligned with the interior chamber, the portion being either cylindrical or conically tapered narrowing toward a direction of the fluid discharge port, the interior chamber wall of the housing being a smooth surface to facilitate waste collection flow to the strainer.

6. The waste collection manifold assembly of claim 1 wherein the at least one inlet port of the housing includes two or more inlet ports.

7. The waste collection manifold assembly of claim 6 wherein the two or more inlet ports are vertically spaced.

8. The waste collection manifold assembly of claim 7 wherein the two or more vertically spaced inlet ports are circumferentially aligned, forming a stacked row of inlet ports.

9. The waste collection manifold assembly of claim 7 wherein the at least one inlet port of the housing includes four inlet ports.

10. The waste collection manifold assembly of claim 1 wherein each of the at least one inlet port has a chamber end extending to the interior chamber wall, the interior chamber wall formed with a smooth interior cylindrical or conical surface and the chamber end of each inlet port being flush to the interior surface of the chamber.

11. The waste collection manifold assembly of claim 1 wherein each of the at least one inlet ports are inclined downwardly relative to a horizontal plane in a downward inclination.

12. The waste collection manifold assembly of claim 11 wherein each of the downward inclinations is 3 degrees or more.

13. The waste collection manifold assembly of claim 1 wherein the radial rows are linear or curved.

14. The waste collection manifold assembly of claim 13 wherein the radial rows of upwardly extending peg projections extend outwardly to an end spaced from the chamber interior surface to form flow channels between the interior chamber wall and the outermost upwardly extending peg projections, a flow channels aligned with the first radial rows being smaller than a flow channel aligned with the second radial rows.

15. The waste collection manifold assembly of claim 1 wherein the adjacent radial rows form tapering flow channels tapering wide at a radially outer end and narrowing toward a radially inner end adjacent to the center opening, the tapering flow channels entrapping debris.

16. The waste collection manifold assembly of claim 1 wherein the plurality of upwardly extending peg projections are round pegs.

17. The waste collection manifold assembly of claim 16 wherein the round pegs are of equal lengths vertically oriented such that the plurality of round pegs form a truncated upper conical shape high at the outer periphery of round pegs and dipping lower toward the center opening.

18. The waste collection manifold assembly of claim 16 wherein the round pegs have a round or circular cross section of an average diameter (d) and a length (L) wherein the round pegs form a substantially rigid debris barrier.

19. The waste collection manifold assembly of claim 1 wherein the center opening extends inwardly through a hollow cylinder, the hollow cylinder fitting into the discharge port, and the strainer further comprises a debris blocking tubular cylindrical net reinforced by a coiled reinforcing member affixed over the central opening.

20. The waste collection manifold assembly of claim 19 wherein the discharge port has an internal locking ring and the hollow cylinder has a split locking ring that complimentarily locks together upon assembly of the strainer to the housing.

21. The waste collection manifold assembly of claim 1 has an assembly of tethered covers comprising a plurality of tethered inlet port covers, one tethered inlet port cover for each of the at least one inlet ports, and a tethered single discharge port cover for sealing the discharge port, the assembly of tethered covers being neatly stacked to a meltable projection on the housing, securing the assembly of tethered covers to the housing.

22. The waste collection manifold assembly of claim 1 further comprises a tamper proof prior-use indicator device, the prior-use indicator device being internally affixed to an interior surface in the interior chamber of the housing, the prior-use indicator device changes color when exposed to moisture; and wherein the housing is clear or at least translucent so a color change is readily observable.

23. The waste collection manifold assembly of claim 22 wherein the prior-use indicator device irreversibly changes from a first color to red upon exposure to moisture.

24. The waste collection manifold assembly of claim 23 wherein the waste collection manifold assembly is sealed upon assembly by end caps and tethered port covers or otherwise packaged to prevent premature exposure to moisture sufficient to prematurely activate the prior-use indicator device.

25. The waste collection manifold assembly of claim 24 wherein the prior-use indicator device has a visible exterior location through the housing which is encircled by a label that is open in the area over the prior-use indicator device to draw attention to a prior-use condition and a single use warning written on the label.

* * * * *